United States Patent
Limbach et al.

(10) Patent No.: US 9,758,461 B2
(45) Date of Patent: Sep. 12, 2017

(54) PROCESS FOR PREPARING AN UNSATURATED CARBOXYLIC ACID SALT USING AN ARYLOXIDE

(71) Applicant: BASF SE, Ludwigshafen (DE)

(72) Inventors: Michael Limbach, Worms (DE); Michael Lejkowski, Neckargemuend (DE); Nuria Huguet Subiela, Heidelberg (DE); Alvaro Gordillo, Heidelberg (DE); Ronald Lindner, Dossenheim (DE); Miriam Bru Roig, Heidelberg (DE); Stephan A. Schunk, Heidelberg-Rohrbach (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/311,011

(22) PCT Filed: May 13, 2015

(86) PCT No.: PCT/EP2015/060536
§ 371 (c)(1),
(2) Date: Nov. 14, 2016

(87) PCT Pub. No.: WO2015/173277
PCT Pub. Date: Nov. 19, 2015

(65) Prior Publication Data
US 2017/0107166 A1   Apr. 20, 2017

(30) Foreign Application Priority Data

May 16, 2014  (EP) .................... 14168616

(51) Int. Cl.
*C07C 51/15*   (2006.01)
(52) U.S. Cl.
CPC .................. *C07C 51/15* (2013.01)
(58) Field of Classification Search
CPC ...................................... C07C 51/15
USPC ........................................ 562/550
See application file for complete search history.

(56) References Cited

FOREIGN PATENT DOCUMENTS

WO   WO 2011/107559 A2   9/2011
WO   WO 2013/098772 A1   7/2013

OTHER PUBLICATIONS

Michael L. Lejkowski et al: "The First Catalytic Synthesis of an Acrylate from C02 and an Alkene—A Rational Approach", Chemistry—A European Journal, vol. 18, No. 44, Sep. 20, 2012 (Sep. 20, 2012), pp. 14017-14025.*
International Search Report issued on Aug. 20, 2015 in PCT/EP2015/060536 filed May 13, 2015.
International Preliminary Report on Patentability and Written Opinion of the International Searching Authority issued on Nov. 22, 2016 in PCT/EP2015/060536 filed May 13, 2015.
Michael L. Lejkowski, et al., "The First Catalytic Synthesis of an Acrylate from $CO_2$ and an Alken—A Rational Approach" Chemistry—A European Journal, vol. 18, No. 44, XP055131168, Sep. 20, 2012, pp. 14017-14025.
Dong Jin, et al., "Effect of Sodium Cation on Metallacycle β-Hydride Elimination in $CO_2$—Ethylene Coupling to Acrylates" Chemistry—A European Journal, vol. 20, No. 11, XP055204659, Mar. 10, 2014, pp. 3205-3211.
David C. Graham, et al., "Production of Acrylic Acid through Nickel-Mediated Coupling of Ethylene and Carbon Dioxides—A DFT Study" Organometallics, vol. 26, No. 27, 2007, pp. 6784-6792.
Heinz Hoberg, et al., "Nickel(O)-Induzierte C-C-Verknüpfung Zwischen Kohlendioxid Und Ethylen Sowie Mono-Oder Di-Substituierten Alkenen" Journal of Organometallic Chemistry, vol. 251, 1983, pp. C51-C53.
Reinald Fischer, et al., "A Key Step in the Formation of Acrylic Acid from $CO_2$ and Ethylene: the Transformation of a Nickelalactone into a Nickel-Acrylate Complex" Chem. Commun., 2006, pp. 2510-2512.
Heinz Hoberg, et al., "Nickel(0)-Induzierte C-C-Verknüpfung Zwischen Alkenen Und Kohlendioxid" Journal of Organometallic Chemistry, vol. 236, 1982, pp. C28-C30.
Heinz Hoberg, et al., "A 1-Oxa-2-Nickela-5-Cyclopentanone from Ethene and Carbon Dioxide: Preparation, Structure, and Reactivity" Angew. Chem. Int. Ed. Engl. vol. 26, No. 8, 1987, pp. 771-773.
Jens Langer, et al., "Low-Valent Nickel and Palladium Complexes with 1,1'-Bis(Phosphanyl)-Ferrocenes: Syntheses and Structures of Acrylic Acid and Ethylene Complexes" Eur. J. Inorg. Chem. 2007, pp. 2257-2264.
U.S. Appl. No. 15/311,012, filed Nov. 14, 2016, Michael Limbach, et al.

* cited by examiner

*Primary Examiner* — Deborah D Carr
(74) *Attorney, Agent, or Firm* — Oblon, McClelland, Maier & Neustadt, L.L.P.

(57) ABSTRACT

Catalytic process for preparing an α,β-ethylenically unsaturated carboxylic acid salt, wherein an alkene and carbon dioxide are reacted in the presence of a carboxylation catalyst and in the presence of a specific aryloxide to obtain the α,β-ethylenically unsaturated carboxylic acid salt, the carboxylation catalyst being a transition metal complex. The process allows for efficient preparation of α,β-ethylenically unsaturated carboxylic acid derivatives from $CO_2$ and an alkene.

24 Claims, No Drawings

PROCESS FOR PREPARING AN UNSATURATED CARBOXYLIC ACID SALT USING AN ARYLOXIDE

The present invention relates to a catalytic process for preparing an α,β-ethylenically unsaturated carboxylic acid salt by catalytic carboxylation of an alkene in the presence of a carboxylation catalyst and in the presence of an aryloxide. More particularly, the invention relates to a process for preparing sodium acrylate by direct carboxylation of ethene with carbon dioxide ($CO_2$). Acrylic acid and derivatives thereof are important industrial chemicals and monomer units for production of water-absorbing resins, called superabsorbents.

The direct addition of $CO_2$ onto ethylene to give acrylic acid is industrially unattractive due to thermodynamic limitations ($\Delta G$=42.7 kJ/mol at 298 K) and the unfavorable equilibrium, which at room temperature is virtually completely to the side of the reactants ($K_{298}$=7×10$^{-7}$). On the other hand, the formation of sodium acrylate and water from $CO_2$, ethylene and sodium hydroxide is thermodynamically favored ($\Delta G$=−56.2 kJ/mol at 298 K, $K_{298}$=7.1×10$^9$). The reaction, however, is kinetically inhibited and therefore requires a homogeneous or heterogeneous carboxylation catalyst (Buntine et al., *Organometallics* 2007, 26, 6784).

The stoichiometric coupling of $CO_2$ and ethene at homogeneous Nickel complexes has been known since more than 30 years (Hoberg et al., *J. Organomet. Chem.* 1983, C51). The formation of nickelalactones as intermediates has been discussed, e.g. by Walther et al. (*Chem. Commun.* 2006, 23, 2510-2512). These do not spontaneously decompose by β-hydride elimination, as according to Walther's initial theory. Many nickelalactones are particularly stable and obtained in the form of solids by stoichiometric coupling of $CO_2$ and ethene (*J. Organomet. Chem.* 1983, C51; *J. Organomet. Chem.* 1982, 236, C28; *Angew. Chem. Int. Ed. Engl.* 1987, 26, 771). Some nickelalactones may even be isolated at room temperature in the form of stable solids (*J. Organomet. Chem.* 1982, 236, C28).

Nickelalactones are hydrolysed by mineral acids to yield a saturated carboxylic acid rather than an α,β-ethylenically unsaturated carboxylic acid.

Buntine et al. (*Organometallics* 2007, 26, 6784) and Walther et al. (*Eur. J. Inorg. Chem.* 2007, 2257) suggest that the initially postulated formation of acrylic acid by β-hydride elimination is energetically unfavored. This also explains for the stability of many nickelalactones. The β-hydride elimination postulated by Walther et al. and the equilibrium between nickelalactone and π-complex has never been realized experimentally.

WO 2011/107559 discloses a process for preparing an alkali metal or alkaline earth metal salt of an α,β-ethylenically unsaturated carboxylic acid, wherein a) an alkene, $CO_2$ and a carboxylation catalyst are converted to an alkene/$CO_2$/carboxylation catalyst adduct, b) the adduct is decomposed to release the carboxylation catalyst with an auxiliary base to give the auxiliary base salt of the α,β-ethylenically unsaturated carboxylic acid, c) the auxiliary base salt of the α,β-ethylenically unsaturated carboxylic acid is reacted to release the auxiliary base with an alkali metal or alkaline earth metal base to give the alkali metal or alkaline earth metal salt of the α,β-ethylenically unsaturated carboxylic acid. The intermediate adduct is cleaved by means of an auxiliary base, for example of a tertiary amine, in order to prepare, in a first step, the ammonium salt of the α,β-ethylenically unsaturated carboxylic acid, which overcomes the fundamental thermodynamic limitation. In a second step, the ammonium cation is exchanged for sodium, for example by treatment with aqueous sodium hydroxide solution. The auxiliary base salt formed in the first step is separated from the reaction medium, e.g. by liquid-liquid phase separation.

Limbach et al. (WO 2013/098772, *Chem. Eur. J.* 2012, 18, 14017-14025) disclose a catalytic process for preparing an alkali metal or alkaline earth metal salt of an α,β-ethylenically unsaturated carboxylic acid, wherein a) a transition metal-alkene complex is reacted with $CO_2$ to give a metallalactone, b) the metallalactone is reacted with a base to give an adduct of the alkali metal or alkaline earth metal salt of the α,β-ethylenically unsaturated carboxylic acid with the transition metal complex, the base being selected from alkali metal or alkaline earth metal hydroxides and alkali metal or alkaline earth metal superbases, and c) the adduct is reacted with an alkene to release the alkali metal or alkaline earth metal salt of the α,β-ethylenically unsaturated carboxylic acid and regenerate the transition metal-alkene complex. In step c), the transition metal-alkene complex is regenerated and is available again for step a). This completes the catalytic cycle. Sodium acrylate was obtained at an overall yield of 1020% (2.55 mmol) based on the Nickel (0.25 mmol). This yield was obtained in a process wherein the reaction conditions were varied in 18 cycles. Each cycle included increasing and decreasing $CO_2$ partial pressure, increasing and decreasing ethene partial pressure, and adding NaOtBu at decreased gas pressure.

Ideally, the base used for deprotonating the metallalactone fulfils the following requirements: Its basicity is sufficient for abstracting the α-hydrogen atom of the metallalactone. It is accompanied by a cation of sufficient Lewis acidity to coordinate to the carboxylic group formed by cleavage of the metallalactone. Finally, the base should not react with carbon dioxide, or the equilibrium between the base and its carbon dioxide-adduct should be at the free base side, allowing for the process to be carried out as a one-pot reaction. The bases proposed hitherto do not equally fulfil all of these requirements.

It is an object of the present invention to provide more efficient catalytic processes for preparing α,β-ethylenically unsaturated carboxylic acid derivatives from $CO_2$, an alkene and a base.

The invention provides a catalytic process for preparing an α,β-ethylenically unsaturated carboxylic acid salt, wherein an alkene and carbon dioxide are reacted in the presence of a carboxylation catalyst and in the presence of an aryloxide to obtain the α,β-ethylenically unsaturated carboxylic acid salt, the carboxylation catalyst being a transition metal complex, wherein the aryloxide corresponds to the general formula (I)

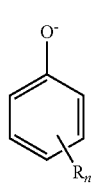

(I)

wherein

R is selected from F, Cl, Br, I, $C_1$-$C_{16}$-alkyl, and $C_3$-$C_{16}$-cycloalkyl, and two vicinal R may constitute a $C_3$-$C_5$-hydrocarbylene bridge that is optionally substituted by one to four substituents which are independently selected from F, Cl, Br, I, $C_1$-$C_{16}$-alkyl, and $C_3$-$C_{16}$-cycloalkyl, and n is an integer selected from 1 to 5, wherein at most two R are F.

Preferably at most one R is F.

The term "transition metal complex" used herein comprises, in a generic manner, all transition metal complexes through which the catalytic cycle is supposed to pass, i.e. transition metal-alkene complexes, metallalactones and adducts wherein the α,β-ethylenically unsaturated carboxylic acid salt coordinates to the transition metal.

In general, the transition metal complex comprises, as the active metal, at least one element of groups 4 (preferably Ti, Zr), 6 (preferably Cr, Mo, W), 7 (preferably Re), 8 (preferably Fe, Ru), 9 (preferably Co, Rh) and 10 (preferably Ni, Pd, Pt) of the Periodic Table of the Elements. Preference is given to nickel, cobalt, iron, rhodium, ruthenium, palladium, platinum, iridium, molybdenum, rhenium, tungsten. Particular preference is given to nickel, palladium, platinum, cobalt, iron, rhodium, ruthenium. Most preferably, the transition metal complex is a nickel or a palladium complex, in particular a nickel complex.

The role of the active metal consists in the activation of $CO_2$ and the alkene in order to form a C—C bond between $CO_2$ and the alkene. It is assumed that a metallalactone is formed within the catalytic cycle from the alkene, carbon dioxide and the transition metal complex. The expression "metallalactone" denotes, according to the exchange nomenclature ("a" nomenclature), a lactone (γ-lactone) in which a carbon atom has been exchanged for a metal atom. The expression "metallalactone" should be interpreted broadly and may comprise compounds with structures similar to the Hoberg complex mentioned at the outset, or related compounds of oligomeric or polymeric structure. The expression shall comprise isolable compounds and (unstable) intermediates.

The metallalactone can be illustrated by the following general formula

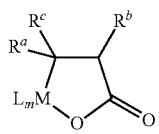

in which

M is the transition metal,

L is a ligand, m is 1 or 2, and $R^a$, $R^b$ and $R^c$ are each independently hydrogen, $C_{1-12}$-alkyl, $C_{2-12}$-alkenyl, or $R^a$ and $R^b$ together with the carbon atoms to which they are bonded are a mono- or diethylenically unsaturated, 5- to 8-membered carbocycle.

It is assumed that the aryloxide deprotonates the metallalactone at the α-carbon atom.

Preferably, the transition metal complex comprises a ligand that coordinates to the transition metal via at least one ligand atom selected from P, N, O, and C.

The ligand preferably comprises at least one phosphorus atom which coordinates to the transition metal. The ligand may be monodentate or polydentate, for example bidentate. In general, two monodentate ligands or one bidentate ligand coordinate to the transition metal. Preferred ligands comprise bulky substituents, as for example the tert-butyl groups in 1,2-bis(di-tert-butylphosphino)ethane or the cyclohexyl groups in 1,2-bis(dicyclohexylphosphino)ethane.

The polydentate, e.g. bidentate, ligand may coordinate to the transition metal to form a four-, five-, six-, seven-, or eight-membered ring, i.e. the transition metal, the atoms which coordinate to the transition metal and the atoms of the shortest chain which connects the atoms coordinating to the transition metal together form a four-, five-, six-, seven-, or eight-membered ring. Ligands that coordinate to the transition metal to form a five-, six-, or seven-membered ring are preferred. Alternatively, the atoms which coordinate to the transition metal may be directly bound to carbon atoms of two cyclopentadienyl ligands bound to a second metal, i.e. iron.

At least one residue is preferably bound via a secondary or tertiary carbon atom to a transition metal coordinating phosphorus atom. More particularly, at least two residues are preferably bound to the phosphorus atom via a secondary or tertiary carbon atom. The term tertiary carbon atom as used herein also includes aromatic carbon atoms. Suitable residues bound to the phosphorus atom via a secondary or tertiary carbon atom are, for example, adamantyl, tert-butyl, sec-butyl, isopropyl, cyclohexyl, cyclopentyl, phenyl, tolyl, xylyl, mesityl, naphthyl, fluorenyl, or anthracenyl, especially tert-butyl, isopropyl, cyclohexyl, or cyclopentyl. At least one residue is preferably bound via a primary carbon atom to a transition metal coordinating phosphorous atom. Suitable residues bound to the phosphorus atom via a primary carbon atom are, for example, methyl, 1-ethyl, 1-propyl, 1-butyl.

Suitable monodentate ligands have, for example, the formula (IIe)

$$PR^{4a}R^{4b}R^{4c} \qquad (IIe)$$

wherein $R^{4a}$, $R^{4b}$, and $R^{4c}$ are independently an unbranched or branched, acyclic or cyclic, aliphatic, araliphatic or aromatic residue having 1 to 16 carbon atoms, where individual carbon atoms may independently be replaced by a hetero group selected from the group of —O— and >N—, individual hydrogen atoms may independently be replaced by Cl, Br, I, or F, and two or all three residues may be covalently bound to one another.

$R^{4a}$, $R^{4b}$, and $R^{4c}$ are preferably independently $C_1$-$C_{12}$-alkyl, $C_3$-$C_{12}$-cycloalkyl, or $C_3$-$C_{14}$-aryl, wherein $C_3$-$C_{12}$-cycloalkyl and $C_3$-$C_{14}$-aryl are unsubstituted or substituted with 1, 2, 3, or 4 substituents independently selected from Cl, Br, I, F, $C_1$-$C_8$-alkyl and $C_1$-$C_4$-alkoxy.

$R^{4a}$, $R^{4b}$, and $R^{4c}$ are most preferably independently methyl, ethyl, 1-propyl, 2-propyl, 1-butyl, 2-butyl, tert-butyl, 1-(2-methyl)propyl, 2-(2-methyl)propyl, 1-pentyl, 1-(2-methyl)pentyl, 1-hexyl, 1-(2-ethyl)hexyl, 1-heptyl, 1-(2-propyl)heptyl, 1-octyl, 1-nonyl, 1-decyl, 1-undecyl, 1-dodecyl, adamantyl, cyclopentyl, methylcyclopentyl, cyclohexyl, methylcyclohexyl, cycloheptyl, cyclooctyl, norbornyl, phenyl, napthyl, tolyl, xylyl, chlorophenyl or anisyl.

Examples of suitable ligands of formula (IIe) are trialkylphosphines, i.e. tri-n-propylphosphine, tri-n-butylphosphine, tri-tert-butylphosphine, trioctylphosphine; tricycloalkylphosphines, i.e. tricyclohexylphosphine, tricyclododecylphosphine; triarylphosphines; i.e. triphenylphosphine, tritolylphosphine, tri(methoxyphenyl)phosphine, trinaphthylphosphine, di-(chlorphenyl)-phenylphosphine; and dialkylarylphosphines, i.e. diethylphenylphosphine, dibutylphenylphosphine.

The ligand is preferably a bidentate P,P; P,N; P,O; or P, carbene ligand, in particular a bidentate P,P ligand. In preferred bidentate P,P ligands, the phosphorous atoms are separated by 2 to 4 bridging atoms that may optionally be part of at least one 5- to 7-membered cyclic substructure.

The phosphorous atoms being "separated by 2 to 4 bridging atoms" means that the shortest chain which connects the coordinating phosphorous atoms comprises 2 to 4 atoms.

In preferred bidentate P,P ligands, wherein the bridging atoms are part of at least one 5- to 7-membered cyclic substructure, each bridging atom directly linked to a P atom, together with the P atom to which it is linked, is part of a 5- to 7-membered cyclic substructure; or two neighbouring bridging atoms are part of a 5- to 7-membered cyclic substructure.

Preferred bidentate P,P ligands are ligands of formula (IIa)

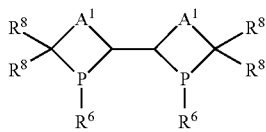

(IIa)

wherein $R^6$ is independently selected from $CHR^7_2$, $CR^7_3$, $C_3$-$C_{10}$-cycloalkyl, and optionally alkylated aryl having 6 to 18 carbon atoms, $R^7$ is independently selected from $C_1$-$C_4$-alkyl, preferably linear $C_1$-$C_4$-alkyl, $A^1$ together with the carbon atoms to which it is bound and the interjacent phosphorous atom forms a 5- to 7-membered cyclic substructure, and $R^8$ is independently selected from hydrogen, $C_1$-$C_{12}$-alkyl, $C_3$-$C_{12}$-cycloalkyl, $C_3$-$C_{12}$-heterocycloalkyl, $C_6$-$C_{14}$-aryl, $C_6$-$C_{14}$-heteroaryl, $C_1$-$C_{12}$-alkoxy, $C_3$-$C_{12}$-cycloalkoxy, $C_3$-$C_{12}$-heterocycloalkoxy, $C_6$-$C_{14}$-aryloxy, and $C_6$-$C_{14}$-heteroaryloxy.

$A^1$ is preferably selected from —$(CR^8_2)_j$— and —$(CR^9=CR^9)_k$— with both $R^9$ being on the same side of the double bond, wherein $R^8$ is independently selected from H, $C_1$-$C_3$-alkyl, and —O—$C_1$-$C_3$-alkyl, $R^9$ is selected from H and $C_1$-$C_3$-alkyl, or at least two $R^9$ constitute a bridge of one of the formulae:

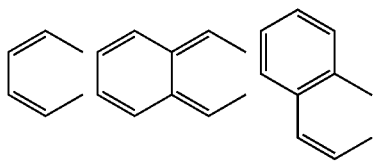

j is 2 or 3, and k is 1 or 2.

$R^6$ is preferably independently selected from $CHR^7_2$, $CR^7_3$, and $C_3$-$C_8$-cycloalkyl, most preferably $CR^7_3$.

$R^7$ is preferably methyl.

$R^8$ is preferably H.

$A^1$ is preferably selected from ethylene, ethenylene, 1,2-phenylene, 1,2-naphthylene, 2,3-naphthylene, and the following formulae

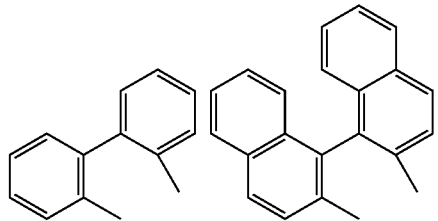

Preferred bidentate P,P ligands are ligands of formula (IIb)

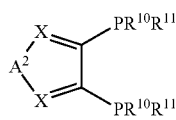

(IIb)

wherein $R^{10}$ is independently selected from linear $C_1$-$C_4$-alkyl, $R^{11}$ is independently selected from $CHR^{10}_2$, $CR^{10}_3$, $C_3$-$C_{10}$-cycloalkyl, and optionally alkylated aryl having 6 to 18 carbon atoms, X is independently selected from C—H, C—$CH_3$, and N, and $A^2$ together with the moieties X to which it is bound and the interjacent carbon atoms forms a 5- to 7-membered cyclic substructure.

$R^{10}$ is preferably independently selected from $C_1$-$C_6$-alkyl and $C_3$-$C_7$-cycloalkyl and $R^{11}$ is $CR^{10}_3$.

$R^{10}$ may, for example, be independently selected from linear $C_1$-$C_4$-alkyl, in particular from linear $C_1$-$C_2$-alkyl.

$R^{11}$ is preferably independently selected from $CHR^{10}_2$, $CR^{10}_3$, and $C_3$-$C_8$-cycloalkyl.

$A^2$ is preferably a —CH=CH— bridge.

X is preferably CH.

Preferred bidentate P,P ligands are ligands of formula (IIc)

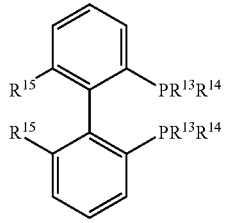

(IIc)

wherein $R^{13}$ and $R^{14}$ are independently selected from $C_3$-$C_{10}$-cycloalkyl, e.g., $C_5$-$C_7$-cycloalkyl, and $R^{15}$ is H, O—$C_1$-$C_6$-alkyl, or both $R^{15}$ together constitute a —CH=CH— bridge.

$R^{15}$ is preferably H or $OCH_3$ and most preferably H.

Preferred bidentate P,P ligands are ligands of formula (IId)

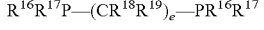

(IId)

wherein $R^{16}$ and $R^{17}$ are independently an unbranched or branched, acyclic or cyclic, aliphatic, araliphatic or aromatic residue having 1 to 16 carbon atoms, where individual carbon atoms may independently be replaced by a hetero group selected from the group of —O— and >N—, individual hydrogen atoms may independently be replaced by Cl, Br, I, or F, and any two residues bound to the same phosphorous atom may be covalently bound to one another, e is 1, 2, 3, 4, or 5, preferably 2, 3, or 4, $R^{18}$ is independently selected from H, $C_1$-$C_8$-alkyl, $C_1$-$C_8$-alkoxy, $C_3$-$C_{10}$-cycloalkyl, $C_3$-$C_{10}$-cycloalkoxy, $C_6$-$C_{10}$-aryl, and $C_6$-$C_{10}$-aryloxy, and $R^{19}$ is independently selected from H, $C_1$-$C_8$-alkyl, $C_3$-$C_{10}$-cycloalkyl, and $C_6$-$C_{10}$-aryl.

Preferably, $(CR^{18}R^{19})_e$ is —$CH_2$—$CH_2$—, —$CH_2$—$CH_2$—$CH_2$—, or —$CH_2$—$CH_2$—$CH_2$—$CH_2$—.

$R^{16}$ and $R^{17}$ are preferably independently $C_1$-$C_{12}$-alkyl, $C_3$-$C_{12}$-cycloalkyl, or $C_3$-$C_{14}$-aryl, wherein $C_3$-$C_{12}$-cycloalkyl and $C_3$-$C_{14}$-aryl are unsubstituted or substituted with 1, 2, 3, or 4 substituents independently selected from Cl, Br, I, F, $C_1$-$C_8$-alkyl and $C_1$-$C_4$-alkoxy.

$R^{16}$ and $R^{17}$ are most preferably independently methyl, ethyl, 1-propyl, 2-propyl, 1-butyl, 2-butyl, tert-butyl, 1-(2-methyl)propyl, 2-(2-methyl)propyl, 1-pentyl, 1-(2-methyl)pentyl, 1-hexyl, 1-(2-ethyl)hexyl, 1-heptyl, 1-(2-propyl)heptyl, 1-octyl, 1-nonyl, 1-decyl, 1-undecyl, 1-dodecyl, adamantyl, cyclopentyl, methylcyclopentyl, cyclohexyl, methylcyclohexyl, cycloheptyl, cyclooctyl, norbornyl, phenyl, napthyl, tolyl, xylyl, chlorophenyl or anisyl.

In a particularly preferred process of the invention, the ligand is selected from 1,2-bis(di-tert-butylphosphino)ethane, 1,2-bis(diisopropylphosphino)ethane, 1,3-bis(diisopropylphosphino)propane, 1,4-bis(diisopropylphosphino)butane, 1,2-bis(tert-butylmethylphosphino)ethane, 1,2-bis(dicyclopentylphosphino)ethane, 1,3-bis(dicyclopentylphosphino)propane, 1,4-bis(dicyclopentylphosphino)butane, 1,2-bis(dicyclohexylphosphino)ethane, 1,3-bis(dicyclohexylphosphino)propane, 1,4-bis(dicyclohexylphosphino)butane,

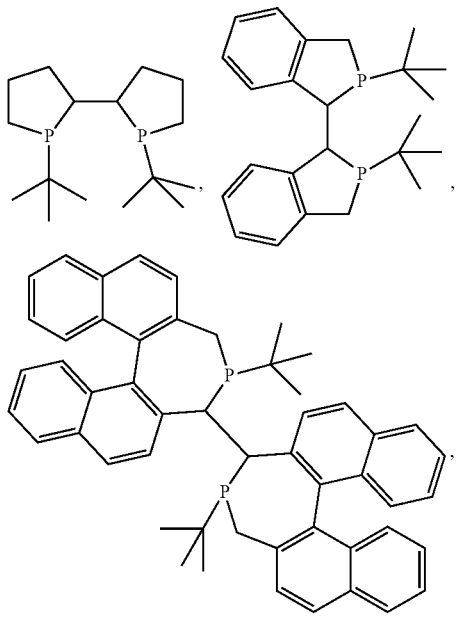

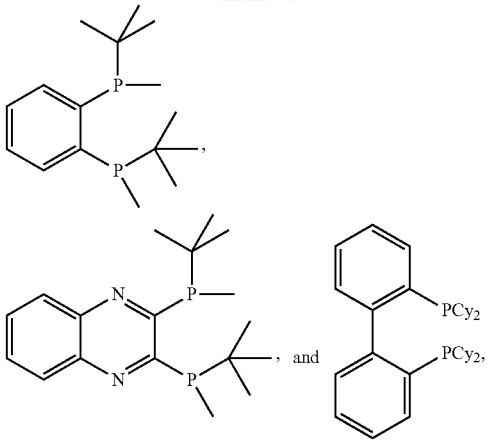

Cy is cyclohexyl.

Suitable monodentate ligands are, for example, monodentate carbene ligands of formula (IIf)

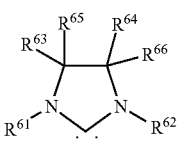

(IIf)

wherein $R^{61}$ and $R^{62}$ are independently an unbranched or branched, acyclic or cyclic, aliphatic, araliphatic or aromatic residue having 1 to 16 carbon atoms, where individual carbon atoms may independently be replaced by a hetero group selected from the group of —O— and >N—, and where individual hydrogen atoms may independently be replaced by Cl, Br, I, or F, $R^{63}$ and $R^{64}$, are independently an unbranched or branched, acyclic or cyclic, aliphatic, araliphatic or aromatic residue having 1 to 16 carbon atoms, where individual carbon atoms may independently be replaced by a hetero group selected from the group of —O— and >N—, individual hydrogen atoms may independently be replaced by Cl, Br, I, or F, and both residues may be covalently bound to one another, and $R^{65}$ and $R^{66}$ together are a chemical bond, or as defined for $R^{63}$ and $R^{64}$.

$R^{61}$ and $R^{62}$ are preferably independently $C_1$-$C_{12}$-alkyl, $C_3$-$C_{12}$-cycloalkyl, or $C_3$-$C_{14}$-aryl, wherein $C_3$-$C_{12}$-cycloalkyl and $C_3$-$C_{14}$-aryl are unsubstituted or substituted with 1, 2, 3, or 4 substituents independently selected from Cl, Br, I, F, $C_1$-$C_8$-alkyl and $C_1$-$C_4$-alkoxy.

$R^{61}$ and $R^{62}$ are most preferably independently methyl, ethyl, 1-propyl, 2-propyl, 1-butyl, 2-butyl, tert-butyl, 1-(2-methyl)propyl, 2-(2-methyl)propyl, 1-pentyl, 1-(2-methyl)pentyl, 1-hexyl, 1-(2-ethyl)hexyl, 1-heptyl, 1-(2-propyl)heptyl, 1-octyl, 1-nonyl, 1-decyl, 1-undecyl, 1-dodecyl, adamantyl, cyclopentyl, methylcyclopentyl, cyclohexyl, methylcyclohexyl, cycloheptyl, cyclooctyl, norbornyl, phenyl, napthyl, tolyl, xylyl, chlorophenyl or anisyl.

Preferably $R^{63}$, $R^{64}$, $R^{65}$ and $R^{66}$ are independently hydrogen, $C_1$-$C_{12}$-alkyl, or $C_1$-$C_{14}$-aryl; or $R^{63}$ and $R^{64}$ are independently hydrogen, $C_1$-$C_{12}$-alkyl, or $C_1$-$C_{14}$-aryl, and $R^{65}$ and $R^{66}$ together are a chemical bond; or $R^{63}$ and $R^{64}$ are independently hydrogen, or methyl, and $R^{65}$ and $R^{66}$ together are a $C_3$-$C_{10}$-alkane-1,3-diyl, $C_3$-$C_{10}$-alkane-1,4-diyl, or $C_3$-$C_{10}$-alkane-1,3-diyl bridge; or $R^{65}$ and $R^{66}$ together are a chemical bond, and $R^{63}$, and $R^{64}$, together with the carbon atoms to which they are bound, are part of a monocyclic or bicyclic aromatic ring system.

Suitable ligands are, for example, bidentate and multidentate ligands that comprise one or two coordinating phosphorous atoms and an additional carbon atom or hetero atom that is bound to the transition metal. Preferably, a 5-membered ring is formed, when the additional carbon atom or hetero atom binds to the transition metal, as for example with (diphenylphosphino)acetate known from the SHOP-Process or with 2-(dimethylphosphino)-N,N-dimethylethanamine. Specific bidentate ligands are ligands of formula (IIg)

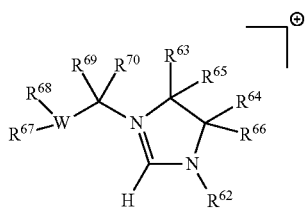

(IIg)

wherein
W is phosphorous (P) or phosphite (P=O),
$R^{62}$, $R^{63}$, $R^{64}$, $R^{65}$ and $R^{66}$ are each as already defined,
$R^{67}$ and $R^{68}$ are as defined for $R^{63}$ and $R^{64}$, and
$R^{69}$ and $R^{70}$ are as defined for $R^{63}$ and $R^{64}$.

Preferably $R^{63}$, $R^{64}$, $R^{65}$ and $R^{66}$ are independently hydrogen, $C_1$-$C_{12}$-alkyl, or $C_1$-$C_{14}$-aryl; or $R^{63}$ and $R^{64}$ are independently hydrogen, $C_1$-$C_{12}$-alkyl, or $C_1$-$C_{14}$-aryl, and $R^{65}$ and $R^{66}$ together are a chemical bond; or $R^{63}$ and $R^{64}$ are independently hydrogen, or methyl, and $R^{65}$ and $R^{66}$ together are a $C_3$-$C_{10}$-alkane-1,3-diyl, $C_3$-$C_{10}$-alkane-1,4-diyl, or $C_3$-$C_{10}$-alkane-1,3-diyl bridge; or $R^{65}$ and $R^{66}$ together are a chemical bond, and $R^{63}$, and $R^{64}$, together with the carbon atoms to which they are bound, are part of a monocyclic or bicyclic aromatic ring system.

$R^{62}$, $R^{67}$ and $R^{68}$ are preferably independently $C_1$-$C_{12}$-alkyl, $C_3$-$C_{12}$-cycloalkyl, or $C_3$-$C_{14}$-aryl, wherein $C_3$-$C_{12}$-cycloalkyl and $C_3$-$C_{14}$-aryl are unsubstituted or substituted with 1, 2, 3, or 4 substituents independently selected from Cl, Br, I, F, $C_1$-$C_8$-alkyl and $C_1$-$C_4$-alkoxy.

$R^{62}$, $R^{67}$ and $R^{68}$ are most preferably independently methyl, ethyl, 1-propyl, 2-propyl, 1-butyl, 2-butyl, tert-butyl, 1-(2-methyl)propyl, 2-(2-methyl)propyl, 1-pentyl, 1-(2-methyl)pentyl, 1-hexyl, 1-(2-ethyl)hexyl, 1-heptyl, 1-(2-propyl)heptyl, 1-octyl, 1-nonyl, 1-decyl, 1-undecyl, 1-dodecyl, adamantyl, cyclopentyl, methylcyclopentyl, cyclohexyl, methylcyclohexyl, cycloheptyl, cyclooctyl, norbornyl, phenyl, napthyl, tolyl, xylyl, chlorophenyl or anisyl.

The ligand may also be a bidentate or multidentate ligand that comprises one or two coordinating nitrogen atoms and an additional carbon atom that is bound to the transition metal. Preferably, a 5-membered ring is formed, when the additional carbon atom binds to the transition metal, as for example with 2-phenylpyridine or 6-phenyl-2,2'-bipyridine.

Suitable tridentate ligands are, for example, ligands of formula (IIh)

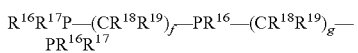

(IIh)

wherein
$R^{16}$, $R^{17}$, $R^{18}$, and $R^{19}$ are each as already defined, and
f and g are independently 1, 2, 3, 4, or 5, preferably 2, 3, or 4.

Exemplary tridentate ligands are ((methylphosphinediyl)bis-(methylene))bis(dimethylphosphine), ((ethylphosphindiyl)bis(methylene))bis(diethyl-phosphine), and ((methylphosphinediyl)bis(methylene))bis(diphenylphosphine).

In addition to the above-described ligands, the transition metal complex may also have at least one further ligand selected from halides, amines, amides, oxides, phosphides, carboxylates, acetylacetonate, aryl- or alkylsulfonates, hydride, CO, olefins, dienes, cycloolefins, nitriles, aromatics and heteroaromatics, ethers, $PF_3$, phospholes, and mono-, di- and polydentate phosphinite, phosphonite, phosphoramidite and phosphite ligands.

Any optional aryloxide and/or further ligand can be displaced when the alkene and carbon dioxide are reacted.

The transition metal complex may for example be obtained from the ligand and the transition metal or from the ligand and a transition metal source comprising the transition metal at oxidation state 0. Alternatively, the transition metal complex may for example be obtained by reducing a salt of the transition metal with a reducing agent, e.g., $H_2$, Mg, Na or Zn.

Useful transition metal sources and salts are commercially available and include, for example $MX_2$, $MX_3$, where X is selected from halide, pseudohalide, carboxylate, alkoxide, carbonate, sulfate, nitrate, hydroxide, acetylacetonate, cyclopentadiene, and the corresponding adducts with solvents such as ethers, DMSO, or water, and M is the active metal of the transition metal complex (e.g. [M(p-cymene)$Cl_2]_2$, [M(benzene)$Cl_2]_n$, [M(COD)$_2$], [M(CDT)], [M($C_2H_4$)$_3$], [$MCl_2 \times H_2O$], [$MCl_3 \times H_2O$], [M(acetylacetonate)$_{1-3}$], [M(DMSO)$_4Cl_2$]).

Palladium sources include, for example, $PdL_2$, $PdL_4$, $LPdX_2$, $L_2PdX_2$, $L_2Pd_2X_2$, $LPd_2X_4$, $Pd_3X_6$, $L_3Pd_2$, $L_2Pd_2$, wherein
X is selected from halide, pseudohalide, carboxylate, alkoxide, carbonate, sulfate, nitrate, hydroxide, acetylacetonate, cyclopentadiene, alkyl, and aryl, and
L is a neutral ligand selected from phosphine, amine, olefin, carbonyl and nitrile,
and the corresponding adducts with solvents such as ethers, DMSO, or water.

The palladium sources and salts are preferably selected from [$Pd_2$(Allyl)$_2$(Cl)$_2$], [$Pd_2$(Methallyl)$_2$(Cl)$_2$][Pd(dba)$_2$], [$Pd_2$(dba)$_3$], $PdCl_2$, $PdBr_2$, $PdI_2$, Pd(NO$_3$)$_2$, PdSO$_4$[Pd(OAc)$_2$], [Pd(PtBu$_3$)$_2$], [Pd(PCy$_3$)$_2$], [Pd(PoTolyl$_3$)$_2$], [Pd(PPh$_3$)$_4$], [Pd(COD)(Cl)(Me)], [Pd(Phen)(OAc)$_2$], [Pd$_2$(PtBu$_3$)$_2$(Br)$_2$], [Pd(C$_6$H$_5$CN)$_2$(CN)$_2$(Cl)$_2$], [Pd(PCy$_3$)$_2$(Cl)$_2$], [Pd(PPh$_3$)$_2$(Cl)$_2$], [Pd(norbornadiene)(Cl$_2$)], [Pd(TMEDA)(Cl)$_2$], [Pd(TMEDA)(CH$_3$)$_2$], [Pd$_3$(OAc)$_6$], [Pd(CF$_3$COO)$_2$], [Pd(Acetylactonate)$_2$] and [Pd(COD)(Cl)$_2$].

Nickel sources and salts include, for example, $NiL_2$, $NiL_4$, $LNiX_2$, $L_2NiX_2$, $L_2Ni_2X_2$ wherein X and L are as defined above and the corresponding adducts with solvents such as ethers, DMSO, or water.

The nickel sources and salts are preferably selected from [Ni(COD)$_2$], NiF$_2$, NiCl$_2$, NiBr$_2$, NiI$_2$, [Ni(OAc)$_2$], [Ni(Acetylactonate)$_2$], [Ni(Ph$_3$P)$_2$(Cl)$_2$], [Ni((PPh$_2$)$_2$Fc)(Cl)$_2$], [Ni$_2$(Methallyl)$_2$(Cl)$_2$], [Ni$_2$(allyl)$_2$(Cl)$_2$], [Ni(CO)$_4$], [Ni(PPh$_3$)$_2$(CO)$_2$], [Ni(NO$_3$)$_2$], [Ni(OH)$_2$], [Ni(PPh$_3$)$_4$], [Ni(CF$_3$COO)$_2$], [Ni(SO$_4$)], [Ni(2-ethylhexanoate)$_2$], [Ni(POPh)$_3$)$_4$], [Ni(C$_7$H$_{15}$COO)$_2$], [Ni(Cp)$_2$], [Ni(PCy$_3$)$_2$], [Ni(PMe$_3$)$_2$(Cl)$_2$], [Ni(PBu$_3$)$_2$(Br)$_2$], and [Ni(dppe)(Cl)$_2$].

Suitable alkenes are those of the following general formula

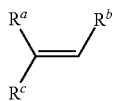

wherein $R^a$, $R^b$ and $R^c$ are each independently hydrogen, $C_{1-12}$-alkyl, $C_{2-12}$-alkenyl, or $R^a$ and $R^b$ together with the carbon atoms to which they are bonded are a mono- or diethylenically unsaturated, 5- to 8-membered carbocycle.

Suitable alkenes are, for example, ethene, propene, isobutene, butadiene, piperylene, 1-butene, 1-pentene, 1-hexene, 1-heptene, 1-octene, 1-nonene, 1-decene, 2-butene, cyclopentene, cyclohexene, cycloheptene, cyclooctene, cyclooctadiene, or styrene. The alkene to be used in the carboxylation is generally gaseous or liquid under the reaction conditions.

In a preferred embodiment, the alkene is ethene. The process according to the invention makes it possible to obtain an acrylate.

In another embodiment, the alkene is piperylene and a sorbate is obtained.

The alkene partial pressure is for example between 0.5 and 200 bar, preferably between 1 and 100 bar, in particular between 2 and 80 bar.

All pressures indicated herein are absolute pressures.

The $CO_2$ for use in the reaction can be used in gaseous, liquid or supercritical form. It is also possible to use carbon dioxide-comprising gas mixtures available on the industrial scale, provided that they are substantially free of carbon monoxide.

$CO_2$ and alkene may also comprise inert gases such as nitrogen or noble gases. Advantageously, however, the content thereof is below 10 mol %, based on the total amount of carbon dioxide and alkene in the reactor.

The carbon dioxide partial pressure is for example between 0.5 and 200 bar, preferably between 2 and 150 bar, in particular between 3 and 100 bar.

The molar ratio of carbon dioxide to alkene in the feed is generally 0.1 to 10 and preferably 0.5 to 5.

Preferably, the ratio of carbon dioxide partial pressure to alkene partial pressure is in the range from 0.1 to 10, for example, in the range from 0.5 to 5, in particular in the range from 1 to 4.

According to the invention, an aryloxide having the general formula (I) below is used to cleave the metallalactone,

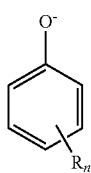

wherein

R is selected from F, Cl, Br, I, $C_1$-$C_{16}$-alkyl, and $C_3$-$C_{16}$-cycloalkyl, and two vicinal R may constitute a $C_3$-$C_5$-hydrocarbylene bridge that is optionally substituted by one to four substituents which are independently selected from F, Cl, Br, I, $C_1$-$C_{16}$-alkyl, and $C_3$-$C_{16}$-cycloalkyl, and n is an integer selected from 1 to 5, wherein at most two R are F.

For example, the $C_3$-$C_5$-hydrocarbylene bridge is an unsaturated $C_4$-hydrocarbylene bridge, preferably with two conjugated double bonds. When the $C_4$-hydrocarbylene bridge has two conjugated double bonds, the aryloxide of formula (I) is a naphthyloxide. The $C_4$-hydrocarbylene bridge is optionally substituted by one to four substituents which are independently selected from F, Cl, Br, I, $C_1$-$C_{16}$-alkyl, and $C_3$-$C_{16}$-cycloalkyl.

In a first aspect of the process according to the invention, the aryloxide does preferably correspond to one of the general formulae (Ia), (Ib), and (Ic)

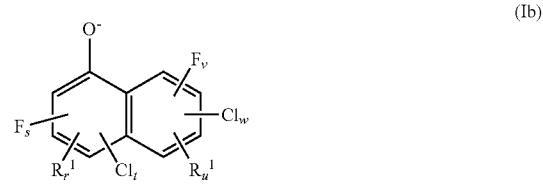

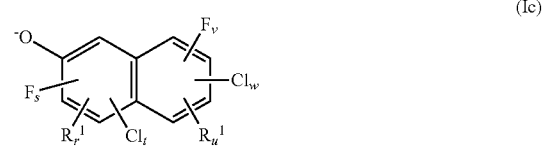

wherein o is 0, 1, 2, or 3, p is 0, 1, or 2, q is 0, 1, or 2, the sum of o, p, and q is at least 1, r, s, t, u, v, and w are 0 or integers, the sum of r and u is 0, 1, 2, or 3, the sum of s and v is 0, 1, or 2, the sum of t and w is 0, 1, or 2, and $R^1$ is selected from Br, I, $C_1$-$C_{16}$-alkyl, and $C_3$-$C_{16}$-cycloalkyl.

Although sodium phenolates are known to be capable of undergoing a Kolbe-Schmitt carboxylation with carbon dioxide under pressure to yield salicylic acid, it has surprisingly been found that the substituted aryloxides of the invention undergo only negligible side reactions.

The chloro and in particular the fluoro substituents have a pronounced negative inductive effect. Aryloxides, wherein the overall negative inductive effect of the aryl substituents does not exceed a certain upper limit are preferred. Accordingly, in formula (Ia), the sum of p and q is preferably at most 3. In formulae (Ib) and (Ic), the sum of s, t, v, and w is preferably at most 3.

Preferably, only one substituent is fluorine. Accordingly, in formula (Ia) p is preferably at most 1. In formulae (Ib) and (Ic), the sum of s and v is preferably at most 1.

Preferably, the total number of fluoro and chloro substituents is limited. In formula (Ia) p is preferably at most 1, q is at most 2, and the sum of p and q is 1 or 2. In formulae (Ib) and (Ic), the sum of s and v is preferably at most 1, the sum of t and w at most 2, and the sum of s, t, v, and w is 1 or 2.

The solubility of the aryloxide in polar and nonpolar phases may be controlled by the length and number of alkyl and cycloalkyl substituents. In general, the solubility in nonpolar phases, for example, in the second liquid phase specified below, is increased when one or multiple alkyl and/or cycloalkyl substituents are comprised by the aryloxide. The aryloxide may for example be substituted by at least one $C_1$-$C_{16}$-alkyl and/or $C_3$-$C_{16}$-cycloalkyl residue, such that its lipophilicity is increased. Accordingly, in one embodiment of the process of the invention, $R^1$ is independently selected from $C_1$-$C_{16}$-alkyl and $C_3$-$C_{16}$-cycloalkyl, for example from $C_3$-$C_{16}$-alkyl and $C_5$-$C_{16}$-cycloalkyl, and preferably from $C_6$-$C_{16}$-alkyl. In formula (Ia) o is preferably 1 or 2, and in formulae (Ib) and (Ic) the sum of r and u is preferably 1, 2 or 3.

In the first aspect of the process according to the invention, the aryloxide may for example correspond to one of the following general formulae (Ia-1), (Ia-2), and (Ia-3)

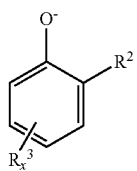

(Ia-1)

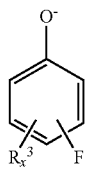

(Ia-2)

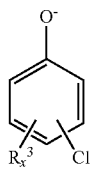

(Ia-3)

wherein
x is 0, 1, or 2,
$R^2$ is methyl, and
$R^3$ is independently $C_1$-$C_{16}$-alkyl or $C_3$-$C_{16}$-cycloalkyl.

Among these, the aryloxides that correspond to the formulae (Ia-2) and (Ia-3) are preferred. x is preferably 1 or 2 in formulae (Ia-2) and (Ia-3).

F is preferably ortho or meta to the oxygen (O⁻ substituent) in the aryloxides that correspond to formula (Ia-2). Aryloxide that corresponds to formula (Ia-2) with F being ortho to O⁻, and x being 1 or 2, preferably 1, is particularly preferred.

The process of the invention is preferably carried out in the presence of alkali metal, alkaline earth metal or zinc cations. Preferred alkali metal cations are Na⁺, Li⁺, and K⁺. Preferred alkaline earth metal cations are $Mg^{2+}$ and $Ca^{2+}$. The process of the invention is most preferably carried out in the presence of sodium cations. The cations are not necessarily fully dissolved in the reaction medium. They may, for example, be bound to anions or be bound to some residue from which the cations are readily released in the form of cations, as for example in lithiumaryls and lithiumalkyls.

The alkali metal, alkaline earth metal or zinc cations may for example be added together with the aryloxide in the form of an alkali metal, alkaline earth metal or zinc salt of the aryloxide.

In the first aspect of the process according to the invention, the aryloxide may for example be selected from sodium 2-fluorophenolate, sodium 3-fluorophenolate, sodium 4-fluorophenolate, sodium 2,6-difluorophenolate, sodium 2,4-difluorophenolate, sodium 2-chlorophenolate, sodium 3-chlorophenolate, sodium 4-chlorophenolate, sodium 2-fluoro-4-methylphenolate, sodium 2-methylphenolate, sodium 2,6-dimethylphenolate, and sodium 1-naphtholate. Sodium 2-fluorophenolate, sodium 3-fluorophenolate, sodium 2-chlorophenolate, sodium 3-chlorophenolate, and sodium 2-fluoro-4-methylphenolate are particularly preferred.

Alternatively, alkali metal or alkaline earth metal cations may be added separately from the aryloxide. In this case, the aryloxide can for example be added in the form of an ammonium aryloxide.

In a preferred second aspect of the process according to the invention, the aryloxide is a phenyloxide wherein the hydrogen atoms at position 2 and position 6 of the phenyl residue are both substituted by a $C_1$-$C_{16}$-alkyl or $C_3$-$C_{16}$-cycloalkyl residue. In the second aspect, the aryloxide thus preferably corresponds to the general formula (I)

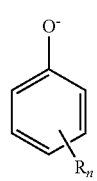

(I)

wherein
R is independently selected from $C_1$-$C_{16}$-alkyl, and $C_3$-$C_{16}$-cycloalkyl,
n is an integer selected from 2 to 5,
and one R is at position 2 and another R is at position 6 of the phenyl ring of general formula (I). This means that both R are at the positions that are ortho to O⁻.

In the second aspect, R may be any primary, secondary or tertiary alkyl residue. R is preferably independently selected from $C_1$-$C_6$-alkyl, for example, from methyl, ethyl, 1-propyl, 2-propyl, 1-butyl, 2-butyl, tert-butyl, most preferably from methyl, 2-propyl, and tert-butyl.

n is preferably 2, 3, or 4, in particular 2 or 3.

Particularly preferred aryloxides of the second aspect of the process according to the invention are selected from 2,6-di-$C_1$-$C_4$-alkyl phenoxides, and 2,6-di-$C_1$-$C_4$-alkyl-4-$C_1$-$C_4$-alkyl phenoxides.

In preferred 2,6-di-$C_1$-$C_4$-alkyl phenoxides, the $C_1$-$C_4$-alkyl residues are preferably independently selected from methyl, 2-propyl, and tert-butyl.

In preferred 2,6-di-$C_1$-$C_4$-alkyl-4-$C_1$-$C_4$-alkyl phenoxides, the number of carbon atoms comprised by any of the alkyl residues at positions 2 and 6 of the phenyl ring is the same as or higher than the number of carbon atoms comprised by the alkyl residue at position 4 of the phenyl ring.

In the second aspect of the process according to the invention, the aryloxide is preferably an alkali metal, alkaline earth metal or zinc aryloxide, most preferably a sodium aryloxide.

Specific examples of aryloxides of the second aspect according to the invention are sodium 2,6-dimethyl phenoxide, sodium 2,6-diisopropyl phenoxide, sodium 2-methyl-6-tert-butyl phenoxide, sodium 2,6-di-tert-butyl phenoxide, sodium 2,6-dimethyl phenoxide, sodium 2,6-dimethyl-4-tert-butyl phenoxide, sodium 2,4,6-trimethyl phenoxide, sodium 2,6-di-tert-butyl-4-methyl phenoxide, sodium 2,6-di-tert-butyl-4-sec-butyl phenoxide, and 2,4,6-tri-tert-butyl phenoxide.

The aryloxide can be added in solid form or as a solution.

The aryloxide is consumed stoichiometrically when the alkene and carbon dioxide are reacted to obtain the α,β-ethylenically unsaturated carboxylic acid salt. The aryloxide is protonated such that its conjugated acid, an arylhydroxide, is obtained as a byproduct. Quantitative consumption of the aryloxide can be prevented by reacting the arylhydroxide with an alkaline material which is capable of deprotonating the arylhydroxide such that the aryloxide is recycled. Accordingly, the process of the invention preferably comprises regenerating the aryloxide by adding an alkaline material.

The amount of aryloxide used in the process according to the invention is generally 5 to 95% by weight, preferably 20 to 60% by weight, and most preferably 5 to 15% by weight, based on the overall reaction medium in the reactor.

It is possible to use the aryloxide in substoichiometric amounts based on the carboxylation catalyst. Even when substoichiometric amounts of aryloxide are used, it is possible to obtain excess α,β-ethylenically unsaturated carboxylic acid salt as based on the catalyst concentration, if the aryloxide is regenerated by addition of the alkaline material.

If an alkaline material is used that is capable of regenerating the aryloxide under the conditions at which the alkene and carbon dioxide are reacted, the alkaline material may be present in the reaction medium while the alkene and carbon dioxide are reacted to the α,β-ethylenically unsaturated carboxylic acid salt. Such alkaline material is for example added into the carboxylation reactor while the alkene and carbon dioxide are reacted.

If the alkaline material is added outside of the carboxylation reactor, i.e. at low carbon dioxide partial pressure, alkaline materials that are inactivated at the conditions of the reaction between alkene and carbon dioxide, i.e. at high carbon dioxide partial pressure, may be used. These alkaline materials include alkali metal or alkaline earth metal hydroxides, oxides, hydrides, and alkoxides.

The alkaline material is for example selected from elemental alkali metal, alkali metal, alkaline earth metal or zinc hydroxides, carbonates, hydrogencarbonates, oxides, alkoxides, hydrides, amides, phosphides, silanolates, alkyls, and aryls.

Suitable alkali metal and alkaline earth metal hydroxides are, for example, sodium hydroxide, potassium hydroxide, magnesium hydroxide and calcium hydroxide.

Suitable carbonates are, for example, lithium carbonate, sodium carbonate, potassium carbonate, calcium carbonate, and zinc carbonate.

Suitable alkali metal hydrogencarbonates are, for example, sodium hydrogencarbonate or potassium hydrogencarbonate.

Suitable alkali metal and alkaline earth metal oxides are, for example, lithium oxide, sodium oxide, calcium oxide and magnesium oxide. Preference is given to sodium hydroxide.

Suitable alkali metal or alkaline earth metal alkoxides are, for example, $C_{1-16}$-alkoxides, preferably $C_{1-12}$-alkoxides, especially $C_{1-4}$-alkoxides. Suitable alkoxides derive from alcohols of the formula $R^{100}OH$. Suitable $R^{100}$ residues are branched or unbranched, acyclic or cyclic alkyl residues having 1-16 carbon atoms, preferably 1-12 carbon atoms, which are unsubstituted or wherein individual carbon atoms may each independently also be replaced by a heteroatom selected from the group of O and >N. Suitable $R^{100}$ residues are benzyl, methyl, ethyl, 1-propyl, 2-propyl, 1-butyl, 2-butyl, 2-(2-methyl)propyl, 1-(2-methyl)propyl, 1-(2-methyl)butyl, 2-(2-methyl)propyl, 1-pentyl, 1-(2-methyl)pentyl, 1-hexyl, 1-(2-ethyl)hexyl, 1-heptyl, 1-(2-propyl)heptyl, 1-octyl, 1-nonyl, 1-decyl, 1-undecyl, 1-dodecyl, $C_3$-$C_{10}$-cycloalkyl which is unsubstituted or may bear a $C_1$-$C_4$-alkyl group, for example cyclopentyl, methylcyclopentyl, cyclohexyl, methylcyclohexyl, cycloheptyl, cyclooctyl. Preferable alkali metal or alkaline earth metal alkoxides are sodium methoxide, sodium ethoxide, sodium isopropoxide, sodium tert-butoxide, and sodium isobutoxide. In the case the alkaline material is an alkoxide, the alcohol from which the alkoxide is obtainable by deprotonation, may serve as the solvent. Sodium tert-butoxide is a preferred alkaline material.

Suitable alkali metal or alkaline earth metal hydrides are, for example, lithium hydride, sodium hydride, potassium hydride, magnesium hydride, and calcium hydride.

Suitable alkali metal or alkaline earth metal amides are, for example, $LiNMe_2$, $LiNEt_2$, $LiN(iPr)_2$, $NaNMe_2$, $NaNEt_2$, $NaN(iPr)_2$, $KNMe_2$, $KNEt_2$, $KN(iPr)_2$, (Me=Methyl; Et=Ethyl; iPr=Isopropyl). The suitable amides also include silicon-containing amides such as sodium hexamethyldisilazide (NaHMDS), potassium hexamethyldisilazide (KHMDS) or lithium hexamethyldisilazide (LiHMDS).

Suitable alkali metal or alkaline earth metal phosphides are, for example, those of the formula $M^2PR^{101}_2$ in which $M^2$ is an alkali metal or an equivalent of an alkaline earth metal, and $R^{101}$ is $C_{1-12}$-alkyl or $C_{6-10}$-aryl, for example $KPPh_2$ or $NaPPh_2$ (Ph=Phenyl).

Suitable alkali metal or alkaline earth metal silanolates are, for example, those of the formula $M^2OSi(C_{1-4}\text{-Alkyl})_3$ in which $M^2$ is an alkali metal or an equivalent of an alkaline earth metal, for example $NaOSiMe_3$.

Suitable alkali metal alkyls or aryls are, for example, lithium alkyl and lithium aryl compounds, such as methyllithium, n-butyllithium, sec-butyllithium, tert-butyllithium, phenyllithium, where the benzene ring may bear substituents at any position (e.g. $OCH_3$, $CH_2NMe_2$, $CONR_2$), cyclohexyllithium, where the cyclohexyl ring may comprise heteroatoms (e.g. O, N, S), ethyllithium, lithium pentadienyl, lithium 2-furanyl, lithium 2-thiophenyl, lithium ethynyl. Also suitable are sodium alkyl and sodium aryl compounds, such as sodium cyclopentadienyl.

The suitable alkaline earth metal alkyls and aryls include magnesium alkyl and magnesium aryl compounds (Grignard reagents) of the general formula $R^{102}MgX$, where $R^{102}$ may be one of the alkyl and aryl residues listed above for the lithium alkyl and lithium aryl compounds and X may be F, Cl, Br, I.

The suitable zinc alkyls and aryls include zinc alkyl and zinc aryl compounds of the general formula $R^{103}ZnX$, where $R^{103}$ may be one of the alkyl and aryl residues listed above for the lithium alkyl and lithium aryl compounds and X may be F, Cl, Br, I.

Suitable alkaline materials are also elemental alkali metals, in particular sodium. The deprotonation of the arylhydroxide is then coupled with a redox reaction. The alkali metal is oxidized to the alkali metal cation and the oxygen-bound proton of the arylhydroxide is reduced to hydrogen.

A particularly preferred alkaline material is sodium hydroxide.

It may happen that part of the carboxylation catalyst is deactivated by oxidation of the active metal. The deactivation reduces the overall efficiency of the process. Preferably a reducing agent is added. Apparently, the reducing agent reactivates the deactivated carboxylation catalyst by a reduction of the oxidized active metal. Thus, the alkene and carbon dioxide are preferably reacted in the presence of a reducing agent. Any reducing agent which is capable of reducing the deactivated carboxylation catalyst is suitable as the reducing agent. Preferable reducing agents are $H_2$, Mg, Na and Zn.

In preferred embodiments, the transition metal complex, and preferably also any intermediate reaction product formed during the reaction of the alkene and carbon dioxide is present in homogeneous solution in the reaction medium in the form of complex-type compounds.

The reaction medium wherein the alkene and carbon dioxide are reacted preferably comprises 0.1 to 20000 ppm by weight, preferably 1 to 1000 ppm by weight, in particular 5 to 500 ppm by weight of transition metal, based on the total weight of the reaction medium.

Preferably, the reaction medium comprises an aprotic organic solvent. Suitable aprotic organic solvents are in principle those which (i) are chemically inert with regard to the carboxylation of the alkene, (ii) in which the aryloxide and the carboxylation catalyst have good solubility, and (iii) which are immiscible or only have limited miscibility with the polar solvent as defined below. Useful aprotic organic solvents are therefore in principle chemically inert, nonpolar solvents, for instance aliphatic, aromatic or araliphatic hydrocarbons, or ethers, for example octane and higher alkanes, benzene, toluene, xylene, chlorobenzene, and anisole. The reaction medium may for example comprise an aprotic organic solvent selected from aromatic hydrocarbons, halogenated aromatic hydrocarbons, alkylated aromatic hydrocarbons, alkanes, ethers, dimethylformamide, dimethyl sulfoxide and mixtures thereof. Examples of suitable ethers are dimethylether, diethylether, di-tert-butylether, di-n-butylether, tetrahydrofuran and 2-methyl-tetrahydrofuran.

Particularly preferred aprotic organic solvents are selected from
cyclic alkyl ethers with 4 to 8 carbon atoms,
dialkyl ethers with 2 to 12 carbon atoms,
cycloalkyl alkyl ethers with 4 to 12 carbon atoms,
aryl alkyl ethers with 7 to 16 carbon atoms,
biaryls with 12 to 16 carbon atoms,
diaryl oxides with 12 to 16 carbon atoms,
$C_1$-$C_8$-alkyl esters of $C_6$-$C_{10}$-aryl monocarboxylic acids,
di-$C_1$-$C_8$-alkyl esters of $C_6$-$C_{10}$-aryl dicarboxylic acids,
dialkyl carbonates with 3 to 13 carbon atoms,
diethers consisting of an dioxyalkylene residue with 2 to 8 carbon atoms and two $C_1$-$C_8$-alkyl residues,
benzenes wherein 1 to 4 hydrogen atoms are substituted by 1 to 4 $C_1$-$C_4$-alkyl residues,
halogenated benzenes,
alkanes with 5 to 18 carbon atoms,
and their mixtures.

The most preferred aprotic organic solvents are selected from tetrahydrofuran, anisole, phenyl butyl ether, dibutyl ether, mixtures of biphenyl and diphenylether, cyclopentyl methyl ether, dibutyl phthalate, butyl benzoate, diethyl carbonate, dibutyl glycol ether, toluene, 2-methyl tetrahydrofuran, monochlorobenzene, and their mixtures.

Albeit the reaction of the alkene and carbon dioxide in the presence of the carboxylation catalyst and in the presence of the aryloxide to obtain the α,β-ethylenically unsaturated carboxylic acid salt is preferably carried out in an aprotic polar solvent, the reaction is tolerant of minor concentrations of polar solvents, in particular, protic polar solvents such as specified below, for example, water. The reaction medium, may thus, for example, contain traces of water or be saturated or partially saturated with water. The term "saturated" refers to the maximum solubility of water in the reaction medium without forming a distinct aqueous phase, at a temperature of 25° C. and pressure of 1 bar. For example, the reaction is tolerant of traces of water up to the water saturation concentration in certain ethers, in particular aryl alkyl ethers with 7 to 16 carbon atoms, e.g., anisole. The water tolerance of the process according to the invention is important, as lower grade and therefore less expensive aprotic organic solvents can be used.

The reactors used may in principle be all reactors which are suitable in principle for gas/liquid reactions or liquid/liquid reactions at the given temperature and the given pressure. Suitable standard reactors for liquid-liquid reaction systems are specified, for example, in K. D. Henkel, "Reactor Types and Their Industrial Application", in Ullmann's Encyclopedia of Industrial Chemistry 2005, Wiley VCH Verlag GmbH & Co KGaA, DOI: 10.1002/14356007.b04_087, chapter 3.3 "Reactors for gas-liquid reactions". Examples include stirred tank reactors, tubular reactors or bubble columns.

The process may be performed as a discontinuous process or as a continuous process. In the discontinuous process, the ligand, the transition metal which may for example be in the form of the transition metal source, the aryloxide, carbon dioxide and the alkene are given into the reactor. Preferably, gaseous carbon dioxide and gaseous alkene are passed into the reactor at the desired pressure. After the reaction has slowed down, the pressure may be reduced.

The process may for example be performed at pressures between 1 and 300 bar, preferably between 1 and 200 bar, in particular between 1 and 150 bar. The process may, for example, be performed at temperatures between −20 and 300° C., preferably between 20 and 250° C., in particular between 40 and 200° C. or between 50 and 180° C., most preferably between 60 and 170° C.

In order to achieve good mixing of the reactants and of the medium comprising the carboxylation catalyst and the aryloxide, suitable apparatuses can be used. Such apparatuses may be mechanical stirrer apparatuses with one or more stirrers, with or without baffles, packed or nonpacked bubble columns, packed or nonpacked flow tubes with or without static mixers, or other useful apparatuses known to those skilled in the art for these process steps. The use of baffles and delay structures is explicitly included in the process according to the invention.

$CO_2$, alkene and the aryloxide can be fed to the reaction medium either together or spatially separately. Such a spatial separation can be accomplished, for example in a stirred tank, in a simple manner by means of two or more separate inlets. When more than one tank is used, for example, there may be different media charges in different tanks. Separation of the addition of the $CO_2$ and alkene reactants in terms of time is also possible in the process according to the invention. Such a time separation can be accomplished, for example, in a stirred tank by staggering the charging with the reactants. In the case of use of flow tubes or apparatus of a similar kind, such charging can be effected, for example, at different sites in the flow tube; such a variation of the addition sites is an elegant way of adding the reactants as a function of residence time. In the process of the present invention, there is no need of separately feeding the $CO_2$, the alkene and the aryloxide to the reaction medium.

One or more immiscible or only partly miscible liquid phases can be used. The optional use of supercritical media and ionic liquids and the establishment of conditions which promote formation of such states are explicitly incorporated into the process. The optional application of phase transfer catalysis and/or the use of surfactants are explicitly incorporated into the process according to the invention.

In a preferred embodiment, the $\alpha,\beta$-ethylenically unsaturated carboxylic acid salt is removed from the reaction medium. The removal of the salt preferably comprises a liquid-liquid phase separation into a first liquid phase in which the $\alpha,\beta$-ethylenically unsaturated carboxylic acid salt is enriched, and a second liquid phase in which the carboxylation catalyst and the aryloxide which may also be in the form of its conjugate acid (arylhydroxide), are enriched. The first and second liquid phases are obtained by bringing the reaction medium which preferably comprises the aprotic organic solvent into contact with a polar solvent, for example, with the polar solvent as specified below, preferably with an aqueous solution, in particular with water.

"Enriched" is understood to mean a partition coefficient P of each of the carboxylation catalyst, the aryloxide and the arylhydroxide of >1.

$$P = \frac{[\text{Concentration of the carboxylation catalyst in the second liquid phase}]}{[\text{Concentration of the carboxylation catalyst in the first liquid phase}]}$$

$$P = \frac{[\text{Concentration of the aryloxide in the second liquid phase}]}{[\text{Concentration of the aryloxide in the first liquid phase}]}$$

$$P = \frac{[\text{Concentration of the arylhydroxide in the second liquid phase}]}{[\text{Concentration of the arylhydroxide in the first liquid phase}]}$$

Each of these partition coefficients is preferably $\geq 10$ and more preferably $\geq 20$, for example, 20 to 1000000.

The second liquid phase preferably comprises an aprotic organic solvent as specified above, in particular an aprotic organic solvent in which the solubility of the aryloxide and its conjugate acid, the arylhydroxide, is high. The aprotic organic solvent is thus preferably selected from the aprotic organic solvents specified above. The aprotic organic solvent is most preferably selected from aromatic aprotic organic solvents, as for example from
 aryl alkyl ethers with 7 to 16 carbon atoms,
 biaryls with 12 to 16 carbon atoms,
 diaryl oxides with 12 to 16 carbon atoms,
 $C_1$-$C_8$-alkyl esters of $C_6$-$C_{10}$-aryl monocarboxylic acids,
 di-$C_1$-$C_8$-alkyl esters of $C_6$-$C_{10}$-aryl dicarboxylic acids,
 benzenes wherein 1 to 4 hydrogen atoms are substituted by 1 to 4 $C_1$-$C_4$-alkyl residues,
 halogenated benzenes,
 and their mixtures;

Most preferably, the aprotic organic solvent comprised by the second liquid phase is selected from anisole, phenyl butyl ether, dibutyl ether, mixtures of biphenyl and diphenylether, dibutyl phthalate, butyl benzoate, toluene, monochlorobenzene, and their mixtures.

The carboxylation catalyst is generally selected by a simple experiment in which the partition coefficient of the desired catalyst is determined experimentally under the planned process conditions.

The liquid-liquid phase separation is preferably promoted by the additional use of a polar solvent in which the $\alpha,\beta$-ethylenically unsaturated carboxylic acid salt has good solubility and which has zero or only limited miscibility with the second liquid phase in which the carboxylation catalyst and the aryloxide are enriched. The polar solvent should be selected such that the polar solvent is present in enriched form in the first liquid phase. "Enriched" is understood to mean a proportion by weight of >50% of the polar solvent in the first liquid phase based on the total amount of polar solvent in both liquid phases. The proportion by weight is preferably >90%, more preferably >95% and most preferably >97%. The polar solvent is generally selected by simple tests in which the partition of the polar solvent in the two liquid phases is determined experimentally under the process conditions.

It is thus preferable to bring the reaction medium, e.g., the crude reaction product, into contact with the polar solvent. The crude reaction product is formed in the reaction underlying the process according to the invention. The crude reaction product usually comprises the carboxylation catalyst, the $\alpha,\beta$-ethylenically unsaturated carboxylic acid salt, the conjugate acid of the aryloxide, i.e. the aryl hydroxide that is formed as a byproduct, and usually some unreacted aryloxide, alkene, carbon dioxide, and the optional aprotic organic solvent.

Preferred substance classes which are suitable as polar solvents are water, alcohols, diols and the carboxylic esters thereof, polyols and the carboxylic esters thereof, sulfones, sulfoxides, open-chain or cyclic amides, and mixtures of the substance classes mentioned.

Examples of suitable alcohols are methanol, ethanol, 1-propanol, isopropanol, tert-butanol and butanol. Examples of suitable diols and polyols are ethylene glycol, diethylene glycol, triethylene glycol, polyethylene glycol, 1,3-propanediol, 2-methyl-1,3-propanediol, 1,4-butanediol, dipropylene glycol, 1,5-pentanediol, 1,6-hexanediol and glycerol.

Examples of suitable sulfoxides are dialkyl sulfoxides, preferably $C_1$- to $C_6$-dialkyl sulfoxides, especially dimethyl sulfoxide.

Examples of suitable open-chain or cyclic amides are formamide, N-methylformamide, N,N-dimethylformamide, N-methylpyrrolidone, acetamide and N-methylcaprolactam.

In a preferred embodiment, the polar solvent is water or an alcohol. In a particularly preferred embodiment, the polar solvent is water, methanol, isopropanol or tert-butanol, most preferably water.

Suitable selection of the aryloxide and optionally of the polar solvent and/or of the aprotic organic solvent which is immiscible or has only limited miscibility therewith, for example, achieves the effect that the carboxylation catalyst, the aryloxide and arylhydroxide is enriched in the second liquid phase. The second liquid phase comprising the carboxylation catalyst, the aryloxide and arylhydroxide can be separated by phase separation from the first liquid phase comprising the α,β-ethylenically unsaturated carboxylic acid salt and be recycled to the reactor without further workup or after regenerating the aryloxide by adding the alkaline material. Owing to the rapid separation of the α,β-ethylenically unsaturated carboxylic acid salt from the catalyst, its decomposition to carbon dioxide and alkene is suppressed. In addition, losses of active metal, aryloxide, and arylhydroxide are minimized, as the catalyst, aryloxide, and arylhydroxide are retained in the second liquid phase.

If desired, traces of water comprised by the second liquid phase can be removed by contacting the second liquid phase with a drying agent. The second liquid phase may, for example, be passed through a column that is filled with the drying agent.

As mentioned above, the reaction underlying the process according to the invention, i.e. the reaction of the alkene and carbon dioxide in the presence of the carboxylation catalyst and in the presence of the aryloxide to obtain the α,β-ethylenically unsaturated carboxylic acid salt, is tolerant of minor concentrations of water.

By appropriate selection of an aprotic organic solvent having incomplete miscibility with water the amount of water remaining physically dissolved in the organic phase after phase separation can be kept low. It is thus possible to recycle the second liquid phase into the carboxylation reactor without removing water dissolved in the second liquid phase. For example, the solubility of water in the aprotic organic solvent at a temperature of 25° C. and a pressure of 1 bar is less than 5%, preferably less than 2%, in particular less than 1% by weight.

To remove the first liquid phase, the procedure may be to only conduct the first liquid phase out of the carboxylation reactor and to leave the second liquid phase within the carboxylation reactor. Alternatively, a liquid-liquid mixed-phase stream can be conducted out of the carboxylation reactor and the liquid-liquid phase separation can be performed in a suitable apparatus outside the carboxylation reactor. The two liquid phases are generally separated by gravimetric phase separation. Suitable examples for this purpose are standard apparatus and standard methods which can be found, for example, in E. Müller et al., "Liquid-Liquid Extraction", in Ullmann's Encyclopedia of Industrial Chemistry, 2005, Wiley-VCH Verlag GmbH & Co. KGaA, DOI: 10.1002/14356007.b03_06, chapter 3 "Apparatus". In general, the first liquid phase enriched with the α,β-ethylenically unsaturated carboxylic acid salt is heavier and forms the lower phase. The second liquid phase can subsequently be recycled into the carboxylation reactor.

In embodiments, wherein the aryloxide is regenerated by adding alkaline material, the alkaline material can, for example, be added to the reaction medium, to the second liquid phase or to any mixture of the first and the second liquid phase. The regeneration of the aryloxide is preferably performed in the liquid or supercritical phase at pressures between 1 and 150 bar, preferably at pressures between 1 and 100 bar, more preferably at pressures between 1 and 60 bar. The temperature may for example be between −20 and 300° C., preferably between 20 and 250° C., more preferably between 40 and 200° C. The reaction conditions at which the aryloxide is regenerated may be the same as or different than those at which the alkene and carbon dioxide are reacted.

If the regeneration of the aryloxide is conducted under the conditions at which the alkene and carbon dioxide are reacted, i.e. in the carboxylation reactor, an alkaline material that is not inactivated under the conditions of the reaction, i.e. an alkali metal or alkaline earth metal hydride, is added.

Regeneration of the aryloxide at a reduced carbon dioxide partial pressure, e.g. a carbon dioxide partial pressure of 0 to 500 mbar, preferably 0 to 100 mbar, i.e. outside of the carboxylation reactor, allows a nucleophilic base such as an alkali metal or alkaline earth metal hydroxide, in particular sodium hydroxide, to be used as the alkaline material. The reaction of the arylhyroxide with the alkali metal or alkaline earth metal hydroxide regenerates the alkali metal or alkaline earth metal aryloxide; an equivalent of water is produced as a by-product. The regeneration of the aryloxide may be driven to completion by removing, i.e. evaporating, water.

The separation of the α,β-ethylenically unsaturated carboxylic acid salt is preferably achieved by phase separation. The alkali metal or alkaline earth metal salt of the α,β-ethylenically unsaturated carboxylic acid can, for example, be separated in a polar aqueous phase from an organic phase. The optional use of supercritical media and ionic liquids, and the establishment of conditions which promote the formation of such states, is explicitly incorporated into the process. Optional changes in temperature and pressure that facilitate the separation of the phases are explicitly included by the process of the invention.

The regeneration of the aryloxide and the phase separation may be carried out together in one step. An aqueous phase comprising the alkaline material, i.e. an aqueous solution of the alkaline material, is preferably added to the reaction medium after the alkene and carbon dioxide have been reacted, such that two phases are formed and the arylhydroxide is reconverted to the aryloxide. Liquid-liquid extraction can be effected in all apparatus suitable for this purpose, such as stirred vessels, extractors or percolators. An aqueous phase is obtained, which comprises an aqueous solution of the alkali metal or alkaline earth metal salt of the α,β-ethylenically unsaturated carboxylic acid, and an organic phase which comprises the aryloxide and the carboxylation catalyst.

One specifc process according to the invention is a continuous process comprising
  a first step that is carried out in a reaction zone, e.g., in a carboxylation reactor, wherein the reaction of the alkene, e.g., ethene, and the carbon dioxide in the presence of the carboxylation catalyst and in the presence of the aryloxide is carried out in the reaction medium comprising the aprotic organic solvent,
    the second liquid phase being recycled from the second step, the alkene, and the carbon dioxide are fed into the reaction zone, and
    the crude reaction product is discharged from the reaction zone; and
  a second step that is carried out in a phase separation zone, e.g., in a liquid-liquid phase separator, wherein
    the crude reaction product obtained from the first step is fed into the phase separation zone,
    the first liquid phase in which the α,β-ethylenically unsaturated carboxylic acid salt is enriched is discharged from the phase separation zone, and
    the second liquid phase in which the carboxylation catalyst, the unconverted aryloxide and the arylhydroxide are enriched, is discharged from the phase separation zone and recycled into the first step with removing some or all of the polar solvent, e.g., water, comprised by the second liquid phase or without removing any of the polar solvent; and
  wherein
  the crude reaction product is mixed with the polar solvent before it is fed into the phase separation zone and/or when it is fed into the phase separation zone, in order to obtain the first liquid phase and the second liquid phase, and the alkaline material, e.g., sodium hydroxide, is added to the crude reaction product that is discharged from the reaction zone and/or into the phase separation zone and/or into the second liquid phase that is discharged from the phase separation zone.

The invention is illustrated in detail by the examples which follow.

In the examples, the following abbreviations are used:
2-MeTHF 2-methyl tetrahydrofuran
DMF dimethylformamide
Ex. Example
ICP-MS Inductively coupled plasma mass spectrometry
Ni(COD)$_2$ bis(cyclooctadiene)nickel(0)
PhCl monochlorobenzene
THF tetrahydrofuran
TON turnover number with respect to transition metal
Cp cyclopentadiene
Cp* pentamethylcyclopentadiene
dtbpe 1,2-bis(di-tert-butylphosphino)ethane
dtbpb 1,4-bis(di-tert-butylphosphino)butane
dcppe 1,2-bis(dicyclopentylphosphino)ethane
dcppp 1,3-bis(dicyclopentylphosphino)propane
dcppb 1,4-bis(dicyclopentylphosphino)butane
dcpe 1,2-bis(dicyclohexylphosphino)ethane
dcpp 1,3-bis(dicyclohexylphosphino)propane
dcpb 1,4-bis(dicyclohexylphosphino)butane
diprpe 1,2-bis(diisopropyl-phosphino)ethane
diprpp 1,3-bis(diisopropyl-phosphino)propane
diprpb 1,4-bis(diisopropyl-phosphino)butane
Ferrocene-1 1-diphenylphosphino-2-diphenylphosphino-4-tert-butyl-cyclopentadienyl-1'-diisopropylphosphino-3'-tert-butyl-cyclopentadienyl iron
Ferrocene-2 1-diphenylphosphino-2-diphenylphosphino-4-tert-butyl-cyclopentadienyl-1'-diphenylphosphino-3'-tert-butyl-cyclopentadienyl iron
Ferrocene-3 1,1'-bis(diisopropylphosphinocyclopentadienyl) iron
Ferrocene-4 1,1'-bis(dicyclohexylphosphinocyclopentadienyl) iron
iPr-MeOBIPHEP 2,2'-bis(diisopropylphosphino)-6,6'-dimethoxy-1,1'-biphenyl
Ph-BPE 1,2-bis-((2R,5R)-diphenylphospholano)ethane
Triphos 1,1,1-tris(diphenylphosphinomethyl)ethane DuanPhos:

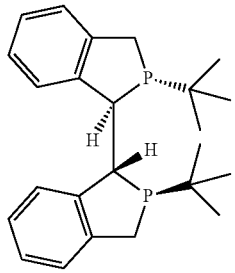

Binapine:

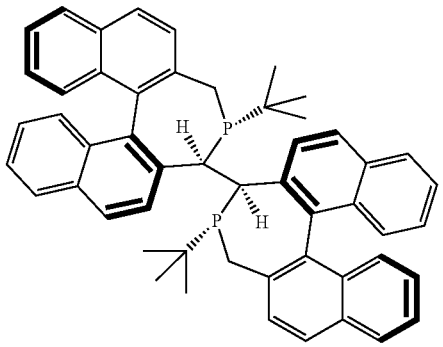

TangPhos:      iPr-DUPHOS:

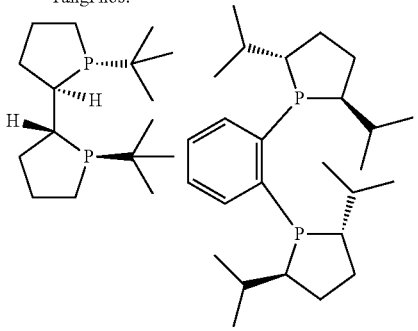

QuinoxP*:      BenzP*:

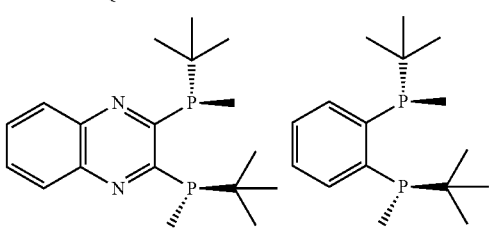

Methyl-DUPHOS:

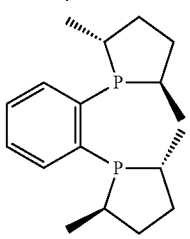

General Procedure

In a glovebox, solvent, transition metal source, ligand, base, and optionally alkaline material, as indicated in or below Tables 1 to 16, were transferred under an argon atmosphere into a charging cartridge sealable by valves at both ends. The volume of the solvent was 30 mL if no other volume is indicated in or below Tables 1 to 16. When Zinc (finely powdered, <10 µm, Sigma Aldrich 209988) was added, it was directly transferred into the autoclave.

The autoclave was charged outside of the glovebox with ethene. One end of the charging cartridge was connected to an inlet port of the autoclave. The other end of the charging cartridge was connected to a nitrogen line. Both valves were opened such that the content of the charging cartridge was transferred into the autoclave. The autoclave was pressurized at room temperature with ethene, and then with carbon dioxide. The equilibration time was 15 minutes with each gas (the partial pressures of $CO_2$ ($p(CO_2)$) and ethene ($p(C_2H_4)$) are indicated below Tables 1 to 16. The solution was stirred at 500 rpm in the autoclave for the time and at the temperature given in or below Tables 1 to 16. The autoclave was cooled to room temperature and opened. The reaction medium was transferred into a glass bottle having a volume of 100 mL. The autoclave was washed with $D_2O$ (15 mL). Internal standard ($NMe_4I$, 25.1 mg, 0.125 mmol, or 2,2,3,3-$d_4$-3-(trimethylsilyl)propionic acid, 28.7 mg, 0.167 mmol, both in 5 mL $D_2O$) was added and the autoclave was washed with additional $D_2O$ (5 mL). All $D_2O$ used for washing the autoclave was combined with the reaction medium. Diethyl ether (40 mL) was added to the combined phases and 2 mL of the aqueous phase were centrifuged in order to improve phase separation. The amount of sodium acrylate was determined by $^1$H-NMR spectroscopy (200 MHz, 70 scans) and the TON determined from the amount of sodium acrylate.

TABLE 1

| Example | Ligand (0.16 mmol) | Aryloxide (3.2 mmol) | TON |
|---|---|---|---|
| 1 | dtbpe | sodium 2-methylphenolate | 1.4 |
| 2 | dtbpe | sodium phenolate | 1.0 |
| 3 | dtbpe | sodium 1-naphtholate | 1.3 |
| 4 | dtbpe | sodium 2-fluorophenolate | 4.6 |
| 5 | dtbpe | sodium 4-fluorophenolate | 3.6 |
| 6 | dtbpe | sodium 4-chlorophenolate | 1.8 |
| 7 | dtbpe | sodium 2,6-difluorophenolate | 1.3 |
| 8 | dtbpe | sodium 2,4,6-trifluorophenolate | 0.8 |
| 9 | dtbpe | sodium 3-fluorophenolate | 5.1 |
| 10 | dtbpe | sodium 3-chlorophenolate | 3.3 |
| 11 | dtbpe | sodium 2,4-difluorophenolate | 1.3 |
| 12 | dtbpe | sodium 2-hydroxyphenolate | 0.6 |
| 13 | dtbpe | disodium salicylate | 0.9 |

Reaction conditions: PhCl, 0.16 mmol Ni(COD)$_2$, p(CO$_2$): 10 bar, p(C$_2$H$_4$): 5 bar, 70° C., 20 h

TABLE 2

| Example | Ligand (0.22 mmol) | Aryloxide (10 mmol) | TON |
|---|---|---|---|
| 14 | BenzP* | sodium 2-methylphenolate | 3.9 |
| 15 | BenzP* | sodium phenolate | 2.7 |
| 16 | BenzP* | sodium 4-fluorophenolate | 2 |
| 17 | BenzP* | sodium 2-fluorophenolate | 9.6 |
| 18 | BenzP* | sodium 3-fluorophenolate | 7.9 |
| 19 | BenzP* | sodium 2,6-difluorophenolate | 0.8 |
| 20 | BenzP* | sodium 2,6-dimethylphenolate | 4 |
| 21 | BenzP* | sodium 2-fluoro-4-methylphenolate | 21 |
| 22 | BenzP* | sodium 2-trifluoromethylphenolate | 0 |

Reaction conditions: THF, 0.2 mmol Ni(COD)$_2$, p(CO$_2$): 10 bar, p(C$_2$H$_4$): 5 bar, 80° C., 20 h The examples of tables 1 and 2 show that the TON is higher with aryloxides that correspond to formula (I), as compared to the TON with aryloxides that do not correspond to formula (I).

TABLE 3

| T [° C.] | DuanPhos | | BenzP* | | dtbpe | | QuinoxP* | | Ferrocene-1 | | iPr-MeOBIPHEP | |
|---|---|---|---|---|---|---|---|---|---|---|---|---|
| | Ex. | TON | Ex. | TON | Ex. | TON | Ex. | TON | Ex. | TON | Ex. | TON |
| 80 | 23 | 21 | 26 | 10 | 29 | 6 | 32 | 11 | 35 | 1 | 38 | 2 |
| 100 | 24 | 24 | 27 | 35 | 30 | 12 | 33 | 14 | 36 | 3 | 39 | 4 |
| 120 | 25 | 21 | 28 | 31 | 31 | 13 | 34 | 7 | 37 | 7 | 40 | 3 |

Reaction conditions: 10 mmol sodium 2-fluorophenolate, 0.22 mmol ligand, THF, 0.2 mmol Ni(COD)$_2$, p(CO$_2$): 10 bar, p(C$_2$H$_4$): 5 bar, 20 h

TABLE 4

| solvent | DuanPhos | | TangPhos | | Binapine | | dtbpe | | BenzP* | |
|---|---|---|---|---|---|---|---|---|---|---|
| | Ex. | TON | Ex. | TON | Ex. | TON | Ex. | TON | Ex. | TON |
| Methanol | 41 | 0 | 46 | 0 | 53 | 0 | 60 | 0 | 67 | 0 |
| DMF | 42 | 5 | 47 | 6 | 54 | 1 | 61 | 2 | 68 | 2 |
| PhCl | 43 | 5 | 48 | 12 | 55 | 9 | 62 | 13 | 69 | 9 |
| Heptane | 44 | 6 | 49 | 10 | 56 | 11 | 63 | 3 | 70 | 7 |
| Dioxane | 45 | 10 | 50 | 11 | 57 | 7 | 64 | 6 | 71 | 13 |
| Toluene | 46 | 15 | 51 | 15 | 58 | 12 | 65 | 6 | 72 | 17 |
| THF | 47 | 16 | 52 | 14 | 59 | 10 | 66 | 9 | 73 | 8 |

Reaction conditions: 10 mmol sodium 3-fluorophenolate, 0.22 mmol ligand, 0.2 mmol Ni(COD)$_2$, p(CO$_2$): 10 bar, p(C$_2$H$_4$): 5 bar, 80° C., 20 h

TABLE 5

| Ex. | Ligand | TON |
|---|---|---|
| 74 | dtbpe | 9.2 |
| 75 | dcpe | 3.9 |
| 76 | iPr-DUPHOS | 1.3 |
| 77 | QuinoxP* | 4.4 |
| 78 | iPr-MeOBIPHEP | 2.9 |
| 79 | Ferrocene-2 | 0.2 |
| 80 | 2,2'-Bis(dicyclohexylphosphino)-1,1'-biphenyl | 11.4 |
| 81 | Triphos | 0.3 |
| 82 | DuanPhos | 15.8 |
| 83 | Methyl-DUPHOS | 1.8 |
| 84 | Ph-BPE | 2 |
| 85 | TangPhos | 13.7 |
| 86 | dcppe × 2 HBF$_4$ | 4.8 |
| 87 | dcppp × 2 HBF$_4$ | 7.5 |
| 88 | 1-di-tert-butylphosphino-2-aminoethane × 2 HBF$_4$ | 0.4 |
| 89 | dtbpb × 2 HBF$_4$ | 0.2 |
| 90 | dcppb × 2 HBF$_4$ | 1.5 |
| 91 | dcpb × 2 HBF$_4$ | 1.3 |
| 92 | dcpp × 2 HBF$_4$ | 4.7 |
| 93 | Ferrocene-3 | 1.1 |
| 94 | Ferrocene-1 | 2 |
| 95 | BenzP* | 8.7 |
| 96 | Bis(diphenylphosphinomethyl)phenylphosphine | 0.7 |
| 97 | 1-di-tert-butylphosphino-2-aminoethane | 0.6 |
| 98 | diprpp | 5.7 |
| 99 | diprpe | 6 |
| 100 | diprpb | 1.8 |
| 101 | Ferrocene-4 | 1.3 |
| 102 | Binapine | 10.4 |

Reaction conditions: 10 mmol sodium 3-fluoro phenolate, 0.22 mmol ligand, THF, 0.2 mmol Ni(COD)$_2$, p(CO$_2$): 10 bar, p(C$_2$H$_4$): 5 bar, 80° C., 20 h

TABLE 6

| Ex. | Equivalents of sodium 2-fluoro phenolate | TON |
|---|---|---|
| 103 | 100 | 93 |
| 104 | 200 | 122 |
| 105 | 300 | 136 |

Reaction conditions: THF, 0.11 mmol BenzP*, 0.1 mmol Ni(COD)$_2$, 10 mmol Zn, p(CO$_2$): 20 bar, p(C$_2$H$_4$): 10 bar, 20 h, 100° C.

TABLE 7

| Ex. | Ligand | TON |
|---|---|---|
| 106 | dtbpe | 2 |
| 107 | QuinoxP* | 0.6 |
| 108 | DuanPhos | 0.3 |
| 109 | iPr-MeOBIPHEP | 0.8 |
| 110 | TangPhos | 8 |
| 111 | Ferrocene-1 | 0.5 |
| 112 | dcpe | 27 |
| 113 | BenzP* | 3.3 |
| 114 | Binapine | 0.9 |
| 115[1] | dcpe | 17 |
| 116 | tri-n-butylphosphine | 0.5 |
| 117 | dcppe × 2 HBF$_4$ | 18 |
| 118 | dcpp × 2 HBF$_4$ | 9 |
| 119 | dcpb × 2 HBF$_4$ | 2 |
| 120 | dcppp × 2 HBF$_4$ | 5 |
| 121 | dcppb × 2 HBF$_4$ | 3 |
| 122 | diprpb | 2 |
| 123[2] | dcpe | 69 |

Reaction conditions:
10 mmol sodium 2-fluorophenolate, 0.22 mmol ligand, THF, 0.2 mmol PdCp*Allyl, p(CO$_2$): 10 bar, p(C$_2$H$_4$): 5 bar, 120° C., 20 h
[1] 10 mmol sodium 2-fluorophenolate, 0.22 mmol ligand, THF, 0.2 mmol CODPdCl$_2$, p(CO$_2$): 10 bar, p(C$_2$H$_4$): 5 bar, 120° C., 20 h, 10 mmol Zn
[2] 10 mmol sodium 2-fluorophenolate, 0.22 mmol ligand, THF, 0.2 mmol CODPdCl$_2$, p(CO$_2$): 20 bar, p(C$_2$H$_4$): 10 bar, 145° C., 20 h, 10 mmol Zn

TABLE 8

| Ex. | Ligand | Aryloxide (10 mmol) | Alkaline material (10 mmol) | Reducing agent (10 mmol) | TON |
|---|---|---|---|---|---|
| 124 | DuanPhos | sodium 2-fluorophenolate | — | — | 28 |
| 125 | DuanPhos | sodium 2-fluorophenolate | NaH | — | 23 |
| 126 | DuanPhos | sodium 2-fluorophenolate | — | Zn | 54 |
| 127 | DuanPhos | sodium 2-fluorophenolate | NaH | Zn | 43 |
| 128 | BenzP* | sodium 2-fluorophenolate | — | — | 65 |
| 129 | BenzP* | sodium 2-fluorophenolate | NaH | — | 73 |
| 130 | BenzP* | sodium 2-fluorophenolate | — | Zn | 77 |
| 131 | BenzP* | sodium 2-fluorophenolate | NaH | Zn | 85 |

Reaction conditions: 0.11 mmol ligand, THF, 0.1 mmol Ni(COD)$_2$, p(CO$_2$): 10 bar, p(C$_2$H$_4$): 5 bar, 100° C., 20 h

TABLE 9

| Ex. | solvent (30 mL) | TON |
|---|---|---|
| 132 | THF | 29 |
| 133 | anisole | 45 |
| 134 | anisole[1] | 39 |
| 135 | phenyl butyl ether | 6 |
| 136 | dibutyl ether | 4 |
| 137 | Dowterm A | 10 |
| 138 | cyclopentyl methyl ether | 3 |
| 139 | dibutyl phtalate | 23 |
| 140 | butyl benzoate | 11 |
| 141 | diethyl carbonate | 11 |
| 142 | dibutyl glycol ether | 12 |

Reaction conditions: 0.2 mmol depe, 20 mmol sodium 2,6-dimethyl phenolate, 1 mmol Zn, 0.2 mmol Pd(COD)Cl$_2$, p(CO$_2$): 20 bar, p(C$_2$H$_4$): 10 bar, 145° C., 20 h
[1] anisole saturated with water

TABLE 10

| Ex. | solvent (30 mL) | TON |
|---|---|---|
| 143 | toluene | 5 |
| 144 | anisole | 60 |
| 145 | dibutyl ether | 3 |
| 146 | dibutyl glycol ehter | 23 |

Reaction conditions: 0.22 mmol depe, 20 mmol sodium 2,6-di-tert-butyl-4-methyl phenolate, 0.2 mmol Pd(Ph$_3$)$_4$, p(CO$_2$): 20 bar, p(C$_2$H$_4$): 10 bar, 145° C., 20 h

TABLE 11

| Ex. | aryloxide (20 mmol) | TON |
|---|---|---|
| 147 | 2,6-dimethyl phenolate sodium | 45 |
| 148 | 2,6-diisopropyl phenolate sodium | 24 |
| 149 | 2-methyl-6-tert-butyl phenolate sodium | 16 |
| 150 | 2,6-di-tert-butyl phenolate sodium | 4 |
| 151 | 2,4,6-trimethyl phenolate sodium | 6 |
| 152 | 2,6-di-tert-butyl-4-methyl phenolate sodium | 7 |

TABLE 11-continued

| Ex. | aryloxide (20 mmol) | TON |
|---|---|---|
| 153 | 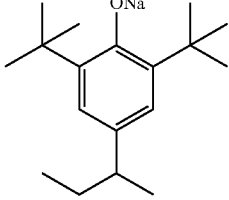 | 3 |
| 154 | 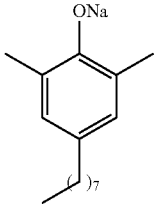 | 2 |
| 155 | 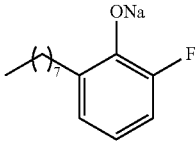 | 5 |

Reaction conditions: 0.22 mmol dcpe, 30 mL anisole, 1 mmol Zn, 0.2 mmol Pd(COD)Cl$_2$, p(CO$_2$): 20 bar, p(C$_2$H$_4$): 10 bar, 145° C., 20 h

TABLE 12

| Ex. | aryloxide (20 mmol) | solvent (30 mL) | TON |
|---|---|---|---|
| 156 | 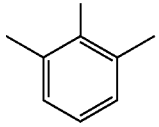 | anisole | 45 |
| 157 | 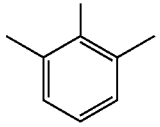 | Dowterm A | 10 |
| 158 | 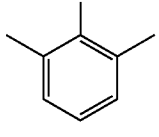 | dibutyl phthalate | 23 |
| 159 | 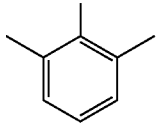 | THF | 29 |
| 160 | 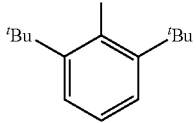 | Dowterm A | 10 |

TABLE 12-continued

| Ex. | aryloxide (20 mmol) | solvent (30 mL) | TON |
|---|---|---|---|
| 161 | 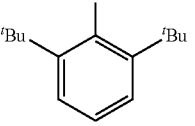 | THF | 22 |
| 162 | 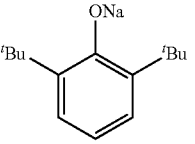 | phenyl butyl ether | 7 |
| 163 | 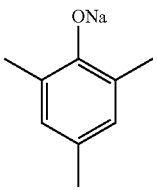 | anisole | 3 |

Reaction conditions: 0.22 mmol dcpe, 1 mmol Zn, 0.2 mmol Pd(COD)Cl$_2$, p(CO$_2$): 20 bar, p(C$_2$H$_4$): 10 bar, 145° C., 20 h

TABLE 13

| Ex. | solvent (30 mL) | aryloxide (20 mmol) | TON |
|---|---|---|---|
| 164 | anisole | 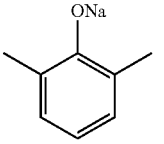 | 45 |
| 165 | anisole[1] | 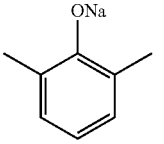 | 39 |
| 166 | anisole | 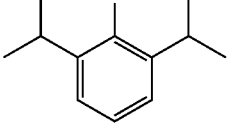 | 24 |
| 167 | anisole[1] | 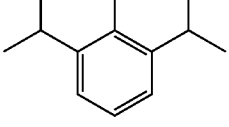 | 30 |
| 168 | 2-MeTHF | 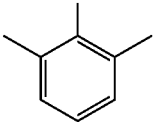 | 12 |

Reaction conditions: 0.22 mmol dcpe, 1 mmol Zn, 0.2 mmol Pd(COD)Cl$_2$, p(CO$_2$): 20 bar, p(C$_2$H$_4$): 10 bar, 145° C., 20 h
[1] anisole saturated with water

TABLE 14

| Ex. | metal source (0.2 mmol) and optinally reducing agent (1 mmol) | aryloxide | TON | aryloxide conversion[3] | aryloxide loss in $D_2O$[4] |
|---|---|---|---|---|---|
| 169[1] | $PdCl_2(COD)/Zn$ | 2,6-di-tert-butyl-phenolate ONa | 4 | 4% | n.d.[5] |
| 170[2] | $Pd(PPh_3)_4$ | | 20 | 40% | |
| 171[1] | $PdCl_2(COD)/Zn$ | 2,6-di-tert-butyl-4-methyl-phenolate ONa | 7 | 7% | low |
| 172[2] | $Pd(PPh_3)_4$ | | 50 | >99% | |
| 173[1] | $PdCl_2(COD)/Zn$ | 2,4,6-tri-tert-butyl-phenolate ONa | n.d. | n.d. | n.d.[5] |
| 174[2] | $Pd(PPh_3)_4$ | | 20 | 40% | |
| 175[1] | $PdCl_2(COD)/Zn$ | 2,6-di-tert-butyl-4-sec-butyl-phenolate ONa | 3 | 3% | low |
| 176[2] | $Pd(PPh_3)_4$ | | 27 | 54% | |

[1] Reaction conditions: 20 mmol aryloxide, 0.22 mmol dcpe, 30 mL THF, 1 mmol Zn, 0.2 mmol Pd(COD)Cl$_2$, p(CO$_2$): 20 bar, p(C$_2$H$_4$): 10 bar, 145° C., 20 h
[2] like [1] but with 10 mmol aryloxide instead of 20 mmol aryloxide.
[3] Base conversion as determined on the basis of the acrylate formed and the amount of base added initially.
[4] The reaction medium was treated as described in the general procedure. The amount of aryloxide [and of the conjugate acid (arylhydroxide)] that was transferred into the water phase was determined after filtration and evaporation of the water phase. The solid residue was dissolved in D$_2$O and $^1$H NMR spectra recorded of the D$_2$O solution thus obtained in order to determine the amount of aryloxide and arylhydroxide transferred into the water phase. While large peaks were observed for the alkene protons of the acrylate, there were no or only very small peaks originating from aliphatic protons (i.e. from the methyl protons of the tert-butyl groups comprised by the aryloxide). This showed, that no or only very little aryloxide and arylhydroxide was transferred into the aqueous phase.
[5] not determined

TABLE 15

| Ex. | ligand | TON | Pd leaching[2] [ppm] |
|---|---|---|---|
| 177[1] | none | 0 | n.d.[3] |
| 178 | $PCy_3$ | 0 | <1 |
| 179 | $Cy_2P\!\!-\!\!\frown\!\!-\!\!PCy_2$ | 106 | 1 |
| 180[1] | $Cy_2P\!\!-\!\!\frown\!\!-\!\!PCy_2$ | 60 | 10 |
| 181 | $Cy_2P\!\!-\!\!\frown\!\!\frown\!\!-\!\!PCy_2$ | 22 | <1 |
| 182 | $Cy_2P\!\!-\!\!\frown\!\!\frown\!\!\frown\!\!-\!\!PCy_2$ | 9 | <1 |
| 183 | 1,1'-bis(dicyclohexylphosphino)ferrocene | 5 | 1 |
| 184 | 1,2-bis(dicyclohexylphosphino)benzene | 7 | 2 |
| 185 | $(C_{14}H_{29})_2P\!\!-\!\!\frown\!\!-\!\!P(C_{14}H_{29})_2$ | 22 | <1 |

Reaction conditions: 0.011 mmol ligand, 10 mmol sodium 2,6-di-tert-butyl-4-methyl phenolate, 0.01 mmol Pd(PPh$_3$)$_4$, 30 mL anisole, p(CO$_2$): 20 bar, p(C$_2$H$_4$): 10 bar, 145° C., 20 h.
[1] 0.22 mmol ligand instead of 0.011 mmol ligand, and 0.2 mmol Pd(PPh$_3$)$_4$ instead of 0.01 mmol Pd(PPh$_3$)$_4$
[2] The reaction medium was treated as described in the general procedure. The amount of palladium leaching into the aqueous phase was determined by ICP-MS.
[3] not determined

TABLE 16

| Ex. | ligand | Zn (mmol) | base | solvent | T (° C.) | TON |
|---|---|---|---|---|---|---|
| 186 | BenzP* | 10 | sodium 2-fluorophenolate (30 mmol) | THF | 120 | 107 |
| 187 | BenzP* | 10 | sodium 2,6-difluorophenolate (30 mmol) | THF | 80 | 1 |
| 188 | BenzP* | 10 | sodium 2-methylphenolate (30 mmol) | THF | 80 | 4 |
| 189 | BenzP* | 10 | sodium 2,6-dimethylphenolate (30 mmol) | THF | 80 | 4 |
| 190 | BenzP* | 10 | sodium 2,6-dimethylphenolate (20 mmol) | THF | 80 | 43 |
| 191 | dcpe | 10 | sodium 2,6-dimethylphenolate (20 mmol) | THF | 145 | 69 |
| 192 | dcpe | 1 | sodium 2,6-dimethylphenolate (20 mmol) | THF | 145 | 57 |
| 193 | dcpe | 0 | sodium 2,6-dimethylphenolate (20 mmol) | THF | 145 | 55 |
| 194 | dcpe | 0 | sodium 2,6-dimethylphenolate (20 mmol) | anisole | 145 | 44 |
| 195 | dcpe | 0 | sodium 2,6-dimethylphenolate (20 mmol) | anisole[1)] | 145 | 22 |
| 196 | dcpe | 0 | Sodium 4-tert-butyl-2,6-dimethylphenolate (10 mmol) | anisole | 145 | 33 |

Reaction conditions: 0.22 mmol ligand, 0.2 mmol Ni(COD)$_2$, p(CO$_2$): 20 bar, p(C$_2$H$_4$): 10 bar, 20 h
[1)] anisole saturated with water The results of tables 1 to 16 show that an efficient catalytic preparation of α,β-ethylenically unsaturated carboxylic acid derivatives from CO$_2$ and an alkene is achieved in the process of the invention.

The invention claimed is:

1. A catalytic process for preparing an α,β-ethylenically unsaturated carboxylic acid salt, the catalytic process comprising reacting an alkene and carbon dioxide in the presence of a carboxylation catalyst and an aryloxide to obtain the α,β-ethylenically unsaturated carboxylic acid salt, wherein:
the carboxylation catalyst is a transition metal complex;
the aryloxide corresponds to formula (I):

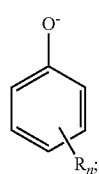

(I)

R is selected from the group consisting of F, Cl, Br, I, a $C_1$-$C_{16}$-alkyl, and a $C_3$-$C_{16}$-cycloalkyl, and two vicinal R groups may constitute a $C_3$-$C_5$-hydrocarbylene bridge that is optionally substituted by one to four substituents which are independently selected from the group consisting of F, Cl, Br, I, a $C_1$-$C_{16}$-alkyl, and a $C_3$-$C_{16}$-cycloalkyl;
n is an integer selected from 1 to 5; and
at most two R groups are F.

2. The catalytic process according to claim 1, wherein two vicinal R groups constitute an unsaturated $C_4$-hydrocarbylene bridge that is optionally substituted by one to four substituents which are independently selected from the group consisting of F, Cl, Br, I, ua $C_1$-$C_{16}$-alkyl, and a $C_3$-$C_{16}$-cycloalkyl.

3. The catalytic process according to claim 1, wherein:
the aryloxide corresponds to one of the formulae (Ia), (Ib), and (Ic):

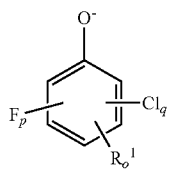

(Ia)

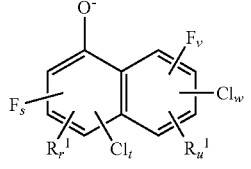

(Ib)

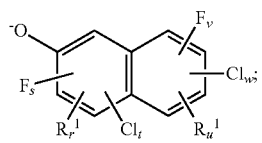

(Ic)

o is 0, 1, 2, or 3;
p is 0, 1, or 2;
q is 0, 1, or 2;
the sum of o, p, and q is at least 1;
r, s, t, u, v, and w are 0 or integers;
the sum of r and u is 0, 1, 2, or 3;
the sum of s and v is 0, 1, or 2;
the sum of t and w is 0, 1, or 2; and
$R^1$ is selected from the group consisting of Br, I, a $C_1$-$C_{16}$-alkyl, and a $C_3$-$C_{16}$-cycloalkyl.

4. The catalytic process according to claim 3, wherein the aryloxide corresponds to the formula (Ia), in which the sum of p and q is at most 3.

5. The catalytic process according to claim 3, wherein:
the aryloxide corresponds to the formula (Ia);
p is at most 1;
q is at most 2; and
the sum of p and q is 1 or 2.

6. The catalytic process according to claim 3, wherein $R^1$ is a $C_1$-$C_{16}$-alkyl or a $C_3$-$C_{16}$-cycloalkyl.

7. The catalytic process according to claim 1, wherein:
the aryloxide corresponds to one of the formulae (Ia-1), (Ia-2), and (Ia-3):

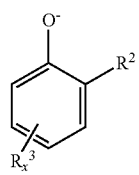
(Ia-1)

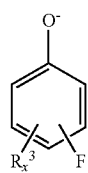
(Ia-2)

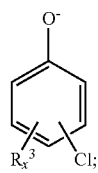
(Ia-3)

x is 0, 1, or 2;
$R^2$ is methyl; and
$R^3$ is independently a $C_1$-$C_{16}$-alkyl or a $C_3$-$C_{16}$-cycloalkyl.

8. The catalytic process according to claim 7, wherein:
the aryloxide corresponds to formula (Ia-2) or (Ia-3); and
x is 1 or 2.

9. The catalytic process according to claim 7, wherein:
the aryloxide corresponds to formula (Ia-2) with F being ortho to $O^-$; and
x is 1 or 2.

10. The catalytic process according to claim 1, wherein the aryloxide is an alkali metal, an alkaline earth metal or a zinc aryloxide.

11. The catalytic process according to claim 1, wherein the aryloxide is selected from the group consisting of sodium 2-fluorophenolate, sodium 3-fluorophenolate, sodium 4-fluorophenolate, sodium 2,6-difluorophenolate, sodium 2,4-difluorophenolate, sodium 2-chlorophenolate, sodium 3-chlorophenolate, sodium 4-chlorophenolate, sodium 2-fluoro-4-methylphenolate, sodium 2-methylphenolate, sodium 2,6-dimethylphenolate, and sodium 1-naphtholate.

12. The catalytic process according to claim 1, wherein the aryloxide is selected from the group consisting of sodium 2-fluorophenolate, sodium 3-fluorophenolate, sodium 2-chlorophenolate, sodium 3-chlorophenolate, and sodium 2-fluoro-4-methylphenolate.

13. The catalytic process according to claim 1, wherein:
R is independently selected from the group consisting of a $C_1$-$C_{16}$-alkyl and a $C_3$-$C_{16}$-cycloalkyl;
n is an integer from 2 to 5; and
one R is at position 2 and another R is at position 6 of the phenyl ring of general formula (I).

14. The catalytic process according to claim 13, wherein:
R is independently a $C_1$-$C_6$-alkyl; and
n is 2 or 3.

15. The catalytic process according to claim 13, wherein the aryloxide is a sodium aryloxide.

16. The catalytic process according to claim 1, wherein the transition metal complex comprises a ligand selected from the group consisting of a bidentate P,P ligand, a bidentate P,N ligand, a bidentate P,O ligand and a P,carbene ligand.

17. The catalytic process according to claim 16, wherein the ligand is a bidentate P,P ligand.

18. The catalytic process according to claim 1, wherein the transition metal complex is a nickel or a palladium complex.

19. The catalytic process according to claim 1, wherein:
the alkene is ethene; and
the α,β-ethylenically unsaturated carboxylic acid is acrylic acid.

20. The catalytic process according to claim 1, wherein the alkene and the carbon dioxide are reacted in the presence of a reducing agent.

21. The catalytic process according to claim 1, wherein the reacting occurs in the presence of a reaction medium comprising an aprotic organic solvent.

22. The catalytic process according to claim 21, wherein the aprotic organic solvent is selected from the group consisting of
a cyclic alkyl ether having 4 to 8 carbon atoms,
a dialkyl ether having 2 to 12 carbon atoms,
a cycloalkyl alkyl ether having 4 to 12 carbon atoms,
an aryl alkyl ether having 7 to 16 carbon atoms,
a biaryl having 12 to 16 carbon atoms,
a diaryl oxide having 12 to 16 carbon atoms,
a $C_1$-$C_8$-alkyl ester of a $C_6$-$C_{10}$-aryl monocarboxylic acid,
a di-$C_1$-$C_8$-alkyl ester of a $C_6$-$C_{10}$-aryl dicarboxylic acid,
a dialkyl carbonate having 3 to 13 carbon atoms,
a diether consisting of an dioxyalkylene residue with 2 to 8 carbon atoms and two $C_1$-$C_8$-alkyl residues,
a benzene wherein 1 to 4 hydrogen atoms are substituted by 1 to 4 $C_1$-$C_4$-alkyl residues,
a halogenated benzene,
an alkane having 5 to 18 carbon atoms, and
mixtures thereof.

23. The catalytic process according to claim 1, wherein:
the reacting occurs in the presence of a reaction medium;
the α,β-ethylenically unsaturated carboxylic acid salt is removed from the reaction medium;
the removal of the α,β-ethylenically unsaturated carboxylic acid salt from the reaction medium comprises a liquid-liquid phase separation into a first liquid phase in which the α,β-ethylenically unsaturated carboxylic acid salt is enriched, and a second liquid phase in which the carboxylation catalyst, unconverted aryloxide and an arylhydroxide byproduct are enriched; and the first and second liquid phases are obtained by contacting the reaction medium with a polar solvent.

24. The catalytic process according to claim 1, further comprising regenerating the aryloxide by adding an alkaline material.

* * * * *